(12) United States Patent
Cooper et al.

(10) Patent No.: US 7,585,517 B2
(45) Date of Patent: *Sep. 8, 2009

(54) TRANSSCLERAL DELIVERY

(75) Inventors: Eugene R. Cooper, Berwyn, PA (US); David M. Kleinman, Rochester, NY (US); Thierry Nivaggioli, Atherton, CA (US); Philippe J M Dor, Cupertino, CA (US); Sreenivasu Mudumba, Union City, CA (US)

(73) Assignee: Macusight, Inc., Union City, CA (US)

( * ) Notice: Subject to any disclaimer, the term of this patent is extended or adjusted under 35 U.S.C. 154(b) by 707 days.

This patent is subject to a terminal disclaimer.

(21) Appl. No.: 10/945,682

(22) Filed: Sep. 20, 2004

(65) Prior Publication Data

US 2005/0064010 A1    Mar. 24, 2005

Related U.S. Application Data

(60) Provisional application No. 60/503,840, filed on Sep. 18, 2003.

(51) Int. Cl.
*A61F 2/00* (2006.01)
*C12P 21/04* (2006.01)
*A61K 38/00* (2006.01)
*A61K 31/44* (2006.01)
*A61K 31/445* (2006.01)

(52) U.S. Cl. ................... 424/428; 435/71.3; 514/12; 514/291; 514/330

(58) Field of Classification Search ............... 424/422, 424/427, 428
See application file for complete search history.

(56) References Cited

U.S. PATENT DOCUMENTS

| | | | |
|---|---|---|---|
| 3,416,530 A | 12/1968 | Ness | |
| 3,630,200 A * | 12/1971 | Higuchi | 424/427 |
| 3,828,777 A | 8/1974 | Ness | |
| 3,914,402 A * | 10/1975 | Shell | 424/428 |
| 3,926,188 A * | 12/1975 | Baker et al. | 424/427 |
| 4,014,335 A | 3/1977 | Arnold | |
| 4,093,709 A | 6/1978 | Choi et al. | |
| 4,300,557 A | 11/1981 | Refojo et al. | |
| 4,316,885 A | 2/1982 | Rakhit | |
| 4,650,803 A | 3/1987 | Stella et al. | |
| 4,853,224 A | 8/1989 | Wong | |
| 4,946,450 A | 8/1990 | Erwin | |
| 4,997,652 A | 3/1991 | Wong | |
| 5,011,844 A | 4/1991 | Fehr | |
| 5,023,262 A | 6/1991 | Caufield et al. | |
| 5,078,999 A | 1/1992 | Warner et al. | |
| 5,100,899 A | 3/1992 | Calne | |
| 5,120,725 A | 6/1992 | Kao et al. | |
| 5,120,727 A | 6/1992 | Kao et al. | |
| 5,120,842 A | 6/1992 | Failli et al. | |
| 5,147,647 A | 9/1992 | Darougar | |
| 5,164,188 A | 11/1992 | Wong | |
| 5,177,203 A | 1/1993 | Failli et al. | |
| 5,178,635 A | 1/1993 | Gwon et al. | |
| 5,189,042 A | 2/1993 | Goulet et al. | |
| 5,192,773 A | 3/1993 | Armistead et al. | |
| 5,258,389 A | 11/1993 | Goulet et al. | |
| 5,300,114 A | 4/1994 | Gwon et al. | |
| 5,322,691 A | 6/1994 | Darougar et al. | |
| 5,368,865 A | 11/1994 | Asakura et al. | |
| 5,378,475 A | 1/1995 | Smith et al. | |
| 5,387,589 A | 2/1995 | Kulkarni | |
| 5,395,618 A * | 3/1995 | Darougar et al. | 424/427 |
| 5,403,901 A | 4/1995 | Namdaran et al. | |
| 5,443,505 A | 8/1995 | Wong et al. | |
| 5,457,111 A | 10/1995 | Luly et al. | |
| 5,466,233 A | 11/1995 | Weiner et al. | |
| 5,514,686 A | 5/1996 | Mochizuki et al. | |
| 5,516,522 A | 5/1996 | Peyman et al. | |
| 5,516,770 A | 5/1996 | Waranis et al. | |
| 5,516,781 A | 5/1996 | Morris et al. | |
| 5,527,907 A | 6/1996 | Or et al. | |
| 5,530,006 A | 6/1996 | Waranis et al. | |
| 5,532,248 A | 7/1996 | Goulet et al. | |
| 5,536,729 A | 7/1996 | Waranis et al. | |
| 5,559,121 A | 9/1996 | Harrison et al. | |
| 5,583,139 A | 12/1996 | Or et al. | |

(Continued)

FOREIGN PATENT DOCUMENTS

CN    1333018    1/2002

(Continued)

OTHER PUBLICATIONS

Bertelmann et al. Ophthamologica 2004; 218: 359-367.*

(Continued)

*Primary Examiner*—Shanon A Foley
(74) *Attorney, Agent, or Firm*—Morrison & Foerster LLP

(57) ABSTRACT

Diseases associated with the tissues in the posterior segment of the eye can be effectively treated by administering therapeutic agents transsclerally to those tissues. Compositions, devices, and methods for delivering therapeutic agents so that they cross the sclera and reach these tissues include injecting solutions or suspensions adjacent to or within the sclera and implanting solid structures containing the therapeutic agent adjacent to or within the sclera. These methods may be used for administering rapamycin or related compounds to treat choroidal neovascularization associated with age-related macular degeneration.

31 Claims, 7 Drawing Sheets

U.S. PATENT DOCUMENTS

| | | | |
|---|---|---|---|
| 5,601,844 A | 2/1997 | Kagayama et al. |
| 5,614,547 A | 3/1997 | Hamilton et al. |
| 5,616,588 A | 4/1997 | Waranis et al. |
| 5,621,108 A | 4/1997 | Smith, III et al. |
| 5,632,984 A | 5/1997 | Wong et al. |
| 5,672,605 A | 9/1997 | Or et al. |
| 5,679,666 A | 10/1997 | Clark |
| 5,696,135 A | 12/1997 | Steiner et al. |
| 5,725,493 A | 3/1998 | Avery et al. |
| 5,743,274 A | 4/1998 | Peyman |
| 5,766,242 A | 6/1998 | Wong et al. |
| 5,766,619 A | 6/1998 | Aiache et al. |
| 5,770,592 A | 6/1998 | Clark |
| 5,773,019 A | 6/1998 | Ashton et al. |
| 5,798,355 A | 8/1998 | Steiner et al. |
| 5,824,072 A | 10/1998 | Wong |
| 5,830,173 A | 11/1998 | Avery et al. |
| 5,883,082 A | 3/1999 | Bennett et al. |
| 5,902,598 A | 5/1999 | Chen et al. |
| 5,904,144 A | 5/1999 | Hammang et al. |
| 5,912,253 A | 6/1999 | Cottens et al. |
| 6,004,973 A | 12/1999 | Guitard et al. |
| 6,007,510 A | 12/1999 | Nigam |
| 6,015,815 A | 1/2000 | Mollison |
| 6,074,661 A | 6/2000 | Olejnik et al. |
| 6,110,485 A | 8/2000 | Olejnik et al. |
| 6,126,687 A | 10/2000 | Peyman |
| 6,142,969 A | 11/2000 | Nigam |
| 6,217,895 B1 | 4/2001 | Guo et al. |
| 6,239,102 B1 | 5/2001 | Tiemessen |
| 6,239,113 B1 | 5/2001 | Dawson et al. |
| 6,254,860 B1 | 7/2001 | Garst |
| 6,258,856 B1 | 7/2001 | Chamberlain et al. |
| 6,306,422 B1 | 10/2001 | Batich et al. |
| 6,326,387 B1 | 12/2001 | Armistead |
| 6,329,386 B1 | 12/2001 | Mollison |
| 6,331,313 B1 | 12/2001 | Wong et al. |
| 6,350,442 B2 | 2/2002 | Garst |
| 6,361,760 B1 | 3/2002 | Murata et al. |
| 6,375,972 B1 | 4/2002 | Guo et al. |
| 6,376,517 B1 | 4/2002 | Ross et al. |
| 6,378,526 B1 | 4/2002 | Bowman et al. |
| 6,387,918 B1 | 5/2002 | Yamanaka et al. |
| 6,397,849 B1 | 6/2002 | Bowman et al. |
| 6,399,629 B1 | 6/2002 | Chamberland et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,440,990 B1 | 8/2002 | Cottens et al. |
| 6,455,518 B2 | 9/2002 | Zenke et al. |
| 6,482,802 B1 | 11/2002 | Hu et al. |
| 6,489,335 B2 | 12/2002 | Peyman |
| 6,534,693 B2 | 3/2003 | Fischell et al. |
| 6,576,224 B1 | 6/2003 | Osbakken et al. |
| 6,617,345 B1 | 9/2003 | Gregory et al. |
| 6,632,836 B1 | 10/2003 | Baker et al. |
| 6,656,460 B2 | 12/2003 | Benita et al. |
| 6,699,493 B2 | 3/2004 | Wong |
| 6,713,081 B2 | 3/2004 | Robinson et al. |
| 6,719,750 B2 | 4/2004 | Varner et al. |
| 6,812,220 B2 | 11/2004 | Jackson et al. |
| 6,864,232 B1 | 3/2005 | Ueno |
| 6,872,383 B2 | 3/2005 | Ueno |
| 6,890,546 B2 | 5/2005 | Mollison et al. |
| 6,939,878 B2 | 9/2005 | Naicker et al. |
| 6,956,043 B2 | 10/2005 | Guitard et al. |
| 7,014,861 B2 | 3/2006 | Roorda et al. |
| 7,018,808 B2 | 3/2006 | Leadlay et al. |
| 7,026,374 B2 | 4/2006 | Nathan et al. |
| 7,033,605 B2 | 4/2006 | Wong |
| 7,034,037 B2 | 4/2006 | Arnold et al. |
| 7,063,857 B1 | 6/2006 | Ueno |
| 7,083,802 B2 * | 8/2006 | Peyman ..................... 424/422 |
| 7,083,803 B2 | 8/2006 | Peyman |
| 7,087,237 B2 | 8/2006 | Peyman |
| 7,128,897 B2 | 10/2006 | Osbakken et al. |
| 7,160,867 B2 | 1/2007 | Abel et al. |
| 7,183,289 B2 | 2/2007 | Zhang et al. |
| 7,186,518 B2 | 3/2007 | Wang et al. |
| 7,223,286 B2 | 5/2007 | Wright et al. |
| 7,402,399 B2 | 7/2008 | Mukherjeei et al. |
| 2002/0187998 A1 | 12/2002 | Ueno |
| 2002/0188282 A1 | 12/2002 | Greenberg |
| 2003/0018044 A1 * | 1/2003 | Peyman ..................... 514/291 |
| 2003/0027744 A1 | 2/2003 | Dana et al. |
| 2003/0044452 A1 | 3/2003 | Ueno |
| 2003/0069232 A1 | 4/2003 | Chiou |
| 2003/0069560 A1 | 4/2003 | Adamis et al. |
| 2003/0077297 A1 | 4/2003 | Chen et al. |
| 2003/0130301 A1 | 7/2003 | Ueno |
| 2003/0171320 A1 | 9/2003 | Guyer |
| 2003/0175324 A1 | 9/2003 | Robinson et al. |
| 2003/0190286 A1 | 10/2003 | Dugger, III |
| 2003/0203892 A1 | 10/2003 | Keller et al. |
| 2004/0018228 A1 | 1/2004 | Fischell et al. |
| 2004/0057958 A1 | 3/2004 | Waggoner, Jr. et al. |
| 2004/0092435 A1 | 5/2004 | Peyman |
| 2004/0167152 A1 | 8/2004 | Rubino et al. |
| 2004/0175428 A1 | 9/2004 | Appel et al. |
| 2004/0180075 A1 | 9/2004 | Robinson et al. |
| 2004/0198763 A1 | 10/2004 | Ueno |
| 2004/0219181 A1 | 11/2004 | Viscasillas |
| 2004/0224394 A1 | 11/2004 | Katz et al. |
| 2004/0234611 A1 | 11/2004 | Ahlheim et al. |
| 2005/0032826 A1 | 2/2005 | Mollison et al. |
| 2005/0042215 A1 | 2/2005 | Owen et al. |
| 2005/0048123 A1 | 3/2005 | Su et al. |
| 2005/0064010 A1 * | 3/2005 | Cooper et al. ................ 424/423 |
| 2005/0074497 A1 | 4/2005 | Schultz |
| 2005/0084514 A1 | 4/2005 | Shebuski et al. |
| 2005/0123605 A1 | 6/2005 | Hunter et al. |
| 2005/0143363 A1 | 6/2005 | De Juan et al. |
| 2005/0187241 A1 * | 8/2005 | Wen et al. ................... 514/291 |
| 2005/0196440 A1 | 9/2005 | Masters et al. |
| 2005/0222191 A1 | 10/2005 | Falotico et al. |
| 2005/0232952 A1 | 10/2005 | Lambert et al. |
| 2005/0249710 A1 | 11/2005 | Wong |
| 2005/0250804 A1 | 11/2005 | Kannan et al. |
| 2005/0255144 A1 | 11/2005 | Schultz |
| 2006/0002971 A1 | 1/2006 | Saltzman et al. |
| 2006/0024350 A1 | 2/2006 | Varner et al. |
| 2006/0034891 A1 | 2/2006 | Lawin et al. |
| 2006/0073182 A1 | 4/2006 | Wong et al. |
| 2006/0182771 A1 | 8/2006 | Dor et al. |
| 2006/0182783 A1 | 8/2006 | Hughes et al. |
| 2006/0198867 A1 | 9/2006 | Toner et al. |
| 2006/0216288 A1 | 9/2006 | Chang |
| 2006/0228393 A1 | 10/2006 | Peyman |
| 2006/0228394 A1 | 10/2006 | Peyman |
| 2006/0247265 A1 | 11/2006 | Clackson et al. |
| 2006/0257450 A1 | 11/2006 | Mudumba et al. |
| 2006/0258698 A1 | 11/2006 | Mudumba et al. |
| 2006/0263409 A1 * | 11/2006 | Peyman ..................... 424/427 |
| 2006/0264453 A1 | 11/2006 | Mudumba et al. |
| 2006/0275218 A1 | 12/2006 | Tamarkin et al. |
| 2007/0014760 A1 | 1/2007 | Peyman |
| 2007/0015697 A1 | 1/2007 | Peyman |
| 2007/0203173 A1 | 8/2007 | Mudumba et al. |
| 2007/0265294 A1 | 11/2007 | Kleinman et al. |

FOREIGN PATENT DOCUMENTS

| | | |
|---|---|---|
| CN | 1340358 | 3/2003 |
| CN | 1456350 | 11/2003 |

| | | | |
|---|---|---|---|
| DE | 40 22 553 A1 | 1/1992 |
| DE | 19810655 A1 | 9/1999 |
| EP | 0041745 A1 | 12/1981 |
| EP | 0041795 A2 | 12/1981 |
| EP | 0467606 A1 | 1/1992 |
| EP | 0904787 A1 | 3/1999 |
| EP | 1142566 A1 | 10/2001 |
| EP | 1126849 B1 | 3/2005 |
| FR | 2382240 | 9/1978 |
| JP | 09-030966 A | 2/1997 |
| JP | 09-315954 A | 12/1997 |
| JP | 10-218787 A | 8/1998 |
| JP | 2001-064198 A | 3/2001 |
| JP | 2002-332225 | 11/2002 |
| RU | 2 123 314 C1 | 12/1998 |
| RU | 2 149 615 C1 | 5/2000 |
| WO | WO-89/01772 A1 | 3/1989 |
| WO | WO-92/05179 A1 | 4/1992 |
| WO | WO-93/19763 A1 | 10/1993 |
| WO | WO-94/05257 A1 | 3/1994 |
| WO | WO-94/21642 A1 | 9/1994 |
| WO | WO-95/14023 A1 | 5/1995 |
| WO | WO-95/26734 A1 | 10/1995 |
| WO | WO-95/28984 A1 | 11/1995 |
| WO | WO-96/36377 A1 | 11/1996 |
| WO | WO-96/40140 A1 | 12/1996 |
| WO | WO-96/41865 A1 | 12/1996 |
| WO | WO-97/10806 A1 | 3/1997 |
| WO | WO-97/16068 A1 | 5/1997 |
| WO | WO-99/07418 A2 | 2/1999 |
| WO | WO-99/07418 A3 | 2/1999 |
| WO | WO-99/11244 A1 | 3/1999 |
| WO | WO-99/20261 A2 | 4/1999 |
| WO | WO-99/22722 A2 | 5/1999 |
| WO | WO-99/34830 A1 | 7/1999 |
| WO | WO-99/37667 A1 | 7/1999 |
| WO | WO-99/45920 A2 | 9/1999 |
| WO | WO-99/45920 A3 | 9/1999 |
| WO | WO-99/58126 A1 | 11/1999 |
| WO | WO-00/06121 A1 | 2/2000 |
| WO | WO-00/09109 A2 | 2/2000 |
| WO | WO-00/09112 A2 | 2/2000 |
| WO | WO-00/09479 A2 | 2/2000 |
| WO | WO-00/28945 A2 | 5/2000 |
| WO | WO-00/33878 A2 | 6/2000 |
| WO | WO-00/37066 A2 | 6/2000 |
| WO | WO-00/37066 A3 | 6/2000 |
| WO | WO-00/38703 A1 | 7/2000 |
| WO | WO-00/40089 A1 | 7/2000 |
| WO | WO-00/56540 A1 | 9/2000 |
| WO | WO-00/66122 A1 | 11/2000 |
| WO | WO-01/28522 A2 | 4/2001 |
| WO | WO-01/30386 A1 | 5/2001 |
| WO | WO-01/42219 A2 | 6/2001 |
| WO | WO-01/47495 A1 | 7/2001 |
| WO | WO-01/93830 A1 | 12/2001 |
| WO | WO-02/28387 A1 | 4/2002 |
| WO | WO-02/062335 A2 | 8/2002 |
| WO | WO-02/066019 A2 | 8/2002 |
| WO | WO-02/074196 A1 | 9/2002 |
| WO | WO-02/100318 A2 | 12/2002 |
| WO | WO-02/100318 A3 | 12/2002 |
| WO | WO-03/017990 A2 | 3/2003 |
| WO | WO-03/017990 A3 | 3/2003 |
| WO | WO-03/051385 A1 | 6/2003 |
| WO | WO-03/068186 A1 | 8/2003 |
| WO | WO-03/074027 A2 | 9/2003 |
| WO | WO-03/074029 A1 | 9/2003 |
| WO | WO-03/090684 A2 | 11/2003 |
| WO | WO-2004/007709 A2 | 1/2004 |
| WO | WO-2004/011000 A1 | 2/2004 |
| WO | WO-2004/014373 A1 | 2/2004 |
| WO | WO-2004/019904 A1 | 3/2004 |
| WO | WO-2004/027027 A1 | 4/2004 |
| WO | WO-2004/028477 A2 | 4/2004 |
| WO | WO-2004/028477 A3 | 4/2004 |
| WO | WO-2004/043480 A2 | 5/2004 |
| WO | WO-2004/043480 A3 | 5/2004 |
| WO | WO-2004/060283 A2 | 7/2004 |
| WO | WO-2004/074445 A2 | 9/2004 |
| WO | WO-2004/096261 A1 | 11/2004 |
| WO | WO-2005/110436 A2 | 11/2004 |
| WO | WO-2005/002625 A2 | 1/2005 |
| WO | WO-2005/011813 A2 | 2/2005 |
| WO | WO-2005/011813 A3 | 2/2005 |
| WO | WO-2005/020962 A1 | 3/2005 |
| WO | WO-2005/027906 A1 | 3/2005 |
| WO | WO-2005/030205 A1 | 4/2005 |
| WO | WO-2005/051452 A2 | 6/2005 |
| WO | WO-2005/055945 A2 | 6/2005 |
| WO | WO-2005/082376 A1 | 9/2005 |
| WO | WO-2005/094279 A2 | 10/2005 |
| WO | WO-2005/099715 A2 | 10/2005 |
| WO | WO-2005/110473 A2 | 11/2005 |
| WO | WO-2006/002365 A2 | 1/2006 |
| WO | WO-2006/002366 A2 | 1/2006 |
| WO | WO-2006/002399 A2 | 1/2006 |
| WO | WO-2006/014484 A2 | 2/2006 |
| WO | WO-2006/020755 A2 | 2/2006 |
| WO | WO-2006/023627 A1 | 3/2006 |
| WO | WO-2006/026531 A1 | 3/2006 |
| WO | WO-2006/039336 A2 | 4/2006 |
| WO | WO-2006/041942 A2 | 4/2006 |
| WO | WO-2006/053007 A2 | 5/2006 |
| WO | WO-2006/086744 A1 | 8/2006 |
| WO | WO-2006/086750 A1 | 8/2006 |
| WO | WO-2006/102378 A1 | 9/2006 |
| WO | WO-2006/108239 A1 | 10/2006 |
| WO | WO-2006/110487 A1 | 10/2006 |
| WO | WO-2006/116716 A2 | 11/2006 |
| WO | WO-2006/133052 A2 | 12/2006 |
| WO | WO-2007/011880 A2 | 1/2007 |
| WO | WO-2007/065588 A1 | 6/2007 |
| WO | WO-2007/083316 A2 | 7/2007 |
| WO | WO-2007/092620 A2 | 8/2007 |
| WO | WO-2007/112052 A2 | 10/2007 |

OTHER PUBLICATIONS

Gardner et al. Current Diabetes Reports. 2008; 8: 263-269.*
Phase I clinical trial from ClinicalTrials.gov.*
Phase II clinical trial from ClinicalTrials.gov.*
Apel, A. et al. (Aug. 1995). "A Subconjuctival Degradable Implant for Cyclosporine Delivery in Corneal Transplant Therapy," *Curr. Eye Res.* 14(8):659-667.
Cicciarelli, N. et al. (Mar. 15, 2001). "Pharmacokinetics of Subconjunctivally Administered Cyclosporine A: Local Delivery Prior to Chemotherapy for Retinoblastoma," *IOVS* 42(4):S332.
Geroski, D. H. et al. (Oct. 31, 2001). "Transscleral Drug Delivery for Posterior Segment Disease," *Adv Drug Deliv Rev.* 52(1):37-48.
Gilbard, J.P. (Feb. 1999). "EW Interview: Electrolyte Balance is Key to Dry-eye Product's Success," *EyeWorld*, pp. 20-21.
Harris, A. et al. (2001). "Implantation of a Sustained-Release Ganciclovir Implant," Chapter 45 in *Vitreoretinal Surgical Techniques*, pp. 521-531.
International Search Report mailed Feb. 4, 2005 for International Application No. PCT/US2004/031025 filed on Sep. 20, 2004, 4 pages.
Kuroki, A. et al. (2003). "Rapamycin Inhibits Retinal and Choroidal Neovascularization in Mice," *ARVO Annual Meeting Abstract Search and Program Planner*, Annual Meeting of the Association for Research in Vision and Ophthalmology, Fort Lauderdale, FL, May 4-8, 2003, Abstract No. 573.
Lallemand, F. et al. (2003). "Cyclosporine A Delivery to the Eye: A Pharmaceutical Challenge," *Euro. J. of Pharm. And Biopharm.* 56:307-318.

Lipner, M. (Feb. 1999). "Dry Eye 1001: Developing Etiologies and Treatments for the Widespread Syndrome," *EyeWorld*, pp. 19-21.

Martin, D.F. et al. (Jan. 15, 1995), "Synergistic Effect of Rapamycin and Cyclosporin A in the Treatment of Experimental Autoimmune Uveroretinitis," *The Journal of Immunology* 154(2):922-927.

Robinson, J.R. et al. (1995). "Bioadhesive and Phase-change Polymers for Ocular Drug Delivery," *Advanced Drug Delivery Reviews* 16:45-50.

Spaide, R.F. et al. (Aug. 2003). "Combined Photodynamic Therapy With Verteporfin and Intravitreal Triamcinolone Acetonide for Choroidal Neovasularization," *Ophthalmology* 110(8):1517-1525.

Wen, R. et al. (2003). "Rapamycin Inhibits Choroidal Neovascularization," *ARVO Annual Meetng Abstract Search and Program Planner*, Annual Meeting of the Association for Research in Vision and Ophthalmology, Fort Lauderdale, FL, May 4-8, 2003, Abstract No. 3928.

Edinger, A. L. et al. (Dec. 1, 2003). "Differential Effects of Rapamycin on Mammalian Target of Rapamycin Signaling Functions in Mammalian Cells," *Cancer Research* 63:8451-8460.

Guba, M. et al. (2001). "Rapamycin Inhibits Tumor Growth and Metastasis by Antiangiogenesis," *Chirurgisches Forum 2001*, pp. 37-39. (English Abstract attached).

Guba, M. et al. (Feb. 2002). "Rapamycin Inhibits Primary and Metastatic Tumor Growth by Antiangiogenesis: Involvement of Vascular Endothelial Growth Factor," *Nature Medicine* 8(2):128-135.

Hackstein, H. et al. (Aug. 1, 2002). "Rapamycin Inhibits Macropinocytosis and Mannose Receptor-Mediated Endocytosis by Bone Marrow-Derived Dendritic Cells," *Blood* 100(3):1084-1087.

Hafizi, S. et al. (2005). "Differential Effects of Rapamycin, Cyclosporine A, and FK506 on Human Coronary Artery Smooth Muscle Cell Proliferation and Signaling," *Vascular Pharmacology* 41:167-176.

Hayward, C. M. et al. (Sep. 22, 1993). "Total Synthesis of Rapamycin via a Novel Titanium-Mediated Aldol Macrocyclization Reaction," *Journal of the American Chemical Society* 115(20):9345-9346.

Humar, R. et al. (2002). "Hypoxia Enhances Vascular Cell Proliferation and Angiogenesis In Virto Via Rapamycin (mTOR)-Dependent Signaling," *The FASEB Journal* 16:771-780.

Kulkarni, P. S. (1994). "Steroidal and Nonsteroidal Drugs in Endotoxin-Induced Uveitis," *Journal of Ocular Pharmacology* 10(1):329-334.

Macular Photocoagulation Study Group. (May 1986). "Argon Laser Photocoagulation for Neovascular Maculopathy, Three-Year Results from Randomized Clinical Trials," *Archives of Ophthalmology* 104:694-701.

Macular Photocoagulation Study Group. (Sep. 1991). "Laser Photocoagulation of Subfoveal Neovascular Lesions in Age-Related Macular Degeneration, Results of a Randomized Clinical Trial," *Archives of Ophthalmology* 109:1220-1231.

Macular Photocoagulation Study Group. (Sep. 1991). "Laser Photocoagulation of Subfoveal Recurrent Neovascular Lesions in Age-Related Macular Degeneration, Results of a Randomized Clinical Trial," *Archives of Ophthalmology* 109:1232-1241.

Macular Photocoagulation Study Group. (Sep. 1991). "Subfoveal Neovascular Lesions in Age-Related Macular Degeneration, Guidelines for Evaluation and Treatment in the Macular Photocoagulation Study," *Archives of Ophthalmology* 109:1242-1257.

Marsland, A. M. et al. (Nov.-Dec. 2002). "The Macrolide Immunosuppressants in Dermatology: Mechanisms of Action," *European Journal of Dermatology* 12:618-621.

Mayhan, W. G. et al. (Sep. 1984). "The Effect of Altering the External Calcium Concentration and a Calcium Channel Blocker, Verapamil, on Microvascular Leaky Sites and Dextran Clearance in the Hamster Cheek Pouch," *Microvascular Research* 28(2):159-179.

MediVas. (2007). "MediVas Announces Signing of Collaboration Agreement with Pfizer," located at <www.medivas.com/News/news_MediVas_Announces_Signing_of_Collaboration_Agreement_with_Pfizer.html> visted on Jul. 28, 2008. (1 page).

Murphy, R. P. (Mar. 1995). "Management of Diabetic Retinopathy," *American Family Physician* 51(4):785-796.

Napoli, K. L. et al. (2001). "From Beach to Bedside: History of the Development of Sirolimus," *Therapeutic Drug Monitoring* 23(5):559-586.

Nicolaou, K. C. et al. (1993). "Total Synthesis of Rapamycin," *Journal of the American Chemical Society* 115(10):4419-4420.

Ohia, E. O. et al. (1992). "Effects of Steroids and Immunosuppressive Drugs on Endotoxin-Uveitis in Rabbits," *Journal of Ocular Pharmacology* 8(4):295-307.

Olsen, T. W. et al. (Nov. 1994). "Rapamycin Inhibits Corneal Allograft Rejection and Neovascularization," *Archives of Ophthalmology* 112:1471-1475.

Paiva, N. L. et al. (Jan.-Feb. 1994). "Incorporation of Acetate, Propionate and Methionine Into Rapamycin by Streptomyces hygroscopicus," *Journal of Natural Products* 54(1):167-177.

Passos, E. et al. (Mar./Apr. 2002). "Ocular Toxcity of Intravitreal Tacrolimus," *Ophthalmic Surgery and Lasers* 33(2):140-144.

Phung, T. L. et al. (Aug. 2006). "Pathological Angiogenesis is Induced by Sustained Akt Signaling and Inhibited by Rapamycin," *Cancer Cell* 10:159-170.

Raghava, S. et al. (Nov. 2004). "Periocular Routes for Retinal Drug Delivery," *Expert Opinion on Drug Delivery* 1(1):99-114.

Renau, T. E. et al. (2003). "Conformationally-Restricted Analogues of Efflux Pump Inhibitors that Potentiate the Activity of Levofloxaxin in *Pseudomonas aeruginosa*," *Bioorganic & Medicinal Chemistry Letters* 13:2755-2758.

Renau, T. E. et al. (2001). "Addressing the Stability of C-Capped Dipeptide Efflux Pump Inhibitors that Potentiate the Activity of Levofloxacin in *Pseudomonas aeruginosa*," *Bioorganic & Medicinal Chemistry Letters* 11:663-667.

Rivera, V. M. et al. (Jul. 1999). "Long-Term Regulated Expression of Growth Hormone in Mice after Intramuscular Gene Transfer," *Proceedings of the National Academy of Sciences of the United States of American* 96:8657-8662.

Romo, D. et al. (1993). "Total Synthesis of (-)-Rapamycin Using an Evans-Tishchenko Fragment Coupling," *Journal of the American Chemical Society* 115(17):7906-7907.

Schlingemann, R. O. et al. (Jun. 1997). "Role of Vascular Permeability Factor/Vascular Endothelial Growth Factor in Eye Disease," *British Journal of Ophthalmology* 81(6):501-512.

Sehgal, S. N. et al. (Apr. 1983). "Demethoxyrapamycin (AY-24,668), A New Antifungal Antibiotic," *The Journal of Antibiotics* 36(4):351-354.

Sehgal, S. N. et al. (Oct. 1975). "Rapamycin (AY-22,989), A New Antifungal Antibiotic, II. Fermentation, Isolation and Characterization," *The Journal of Antibiotics* 28(10):727-732.

Shen, W.-Y. et al. (Jul. 2001). "Combined Effect of Cyclosporine and Sirolimus on Improving the Longevity of Recombinat Adenovirus-Mediated Transgene Expression in the Retina," Archives of Ophthalmology 119:1033-1043.

Simamora, P. et al. (Feb. 1, 2001). "Solubilization of Rapamycin," *International Journal of Pharmaceutics* 213(1-2):25-29.

Stepkowski, S. M. et al. (Jan. 1991). "Rapamycin, a Potent Immunosuppressive Drug for Vascularized Heart, Kidney, and Small Bowel Transplantation in the Rat," *Transplantation* 51(1):22-26.

Treatment of Age-Related Macular Degeneration with Photodynamic Therapy (TAP) Study Group. (Oct. 1999). "Photodynamic Therapy of Subfoveal Choroidal Neovascularization in Age-Related Macular Degeneration With Verteporfin, One-Year Results of 2 Randomized Clinical Trials-TAP Report 1," *Archives of Ophthalmology* 117:1329-1345.

Treatment of Age-Related Macular Degeneration with Photodynamic Therapy (TAP) Study Group. (Apr. 2000). Correction for "Photodynamic Therapy of Subfoveal Choroidal Neovascularization in Age-Related Macular Degeneration with Verteporfin, One-Year Results of 2 Randomized Clinical Trials-TAP Report 1," *Archives of Ophthalmology* 118:488.

Treins, C. et al. (Aug. 2, 2000). "Insulin Stimulates Hypoxia-Inducible Factor 1 Through a Phosphatidylinositol 3-kinase/Target of Rapamycin-Dependent Signaling Pathway," *The Journal of Biological Chemistry* 277(31):27975-27981.

Vézina, C. et al. (Oct. 1975). "Rapamycin (AY-22,989), A New Antifungal Antibiotic, I. Taxonomy of the Producing Streptomycete and Isolation of the Active Principle," *The Journal of Antibiotics* 28(10):721-726.

Akselband, Y. et al. (Dec. 1991). "Rapamycin Inhibits Spontaneous and Fibroblast Growth Factor Beta-Stimulated Proliferation of Endothelial Cells and Fibroblasts," *Transplantation Proceedings* 23(6):2833-2836.

Alteheld, A. et al. (2005). "Biodegradable Amorphous Copolyester-Urethane Networks Having Shape-Memory Properties," *Angewandte Chemie International Edition* 44:1188-1192.

Aramoto, H. et al. (Oct. 2004). "Vascular Endothelial Growth Factor Stimulates Differential Signaling Pathways in In Vivo Microcirculation," *American Journal of Physiology—Heart and Circulatory Physiology* 287:H1590-H1598.

Auricchio, A. et al. (Aug. 2002). "Pharmacological Regulation of Protein Expression from Adeno-Assoicated Viral Vectors in the Eye," *Molecular Therapy* 6(2):238-242.

Bainbridge, J. W. B. et al. (2003). "Hypoxia-Regulated Transgene Expression in Experimental Retinal Choroidal Neovascularization," *Gene Therapy* 10:1049-1054.

Beeley, N. R. F. et al. (Mar. 15, 2006). "Development, Implantation, In Vivo Elution, and Retrieval of a Biocompatible, Sustained Release Subretinal Drug Delivery System." *Journal of Biomedical Materials Research Part A* 76A:690-698.

Behl, C. (Dec. 1997). "Amyloid Beta-Protein Toxicity and Oxidative Stress in Alzheimer's Disease," *Cell & Tissue Research* 290(3):471-480.

Bergers, G. et al. (Jun. 2003). "Tumorigenesis and the Angiogenic Switch," *Nature Reviews-Cancer* 3(6):401-410.

Bourne, R. R. et al., (1998). "Epidemic Optic Neuropathy in Primary School Children in Dar es Salaam, Tanzania," *British Journal of Ophthalmology* 82:232-234.

Bucci, M. et al. (Dec. 2000). "In Vivo Delivery of the Caveolin-1 Scaffolding Domain Inhibits Nitric Oxide Synthesis and Reduces Inflammation," *Nature Medicine* 6(12):1362-1367.

Cancer Weekly Editors. (Jan. 14, 2003). "Cancer Therapy: Study of Possible Anticancer Drug Reveals New Mechanism of Gene Regulation," *Cancer Weekly via NewsRx.com and NewsRx.net*, 2 pages.

Arias, L. (2007). "Management of Diabetic Macular Edema with Antiangiogenic Therapy," *Expert Review of Ophthalmology* 2(1):23-26.

Averbukh, E. et al. (Feb. 2006). "Diabetic Macular Edema: Towards Therapy Aimed at the Underlying Pathogenic Mechanisms," *The Israel Medical Association Journal* 8:127-128.

Ciulla, T. A. et al. (Sep. 2003). "Diabetic Retinopathy and Diabetic Macular Edema: Pathophysiology, Screening, and Novel Therapies," *Diabetes Care* 26(9):2653-2664.

Ciulla. T. A. et al. (Sep.-Oct. 1998). "Age-Related Macular Degeneration: A Review of Experimental Treatments," *Survey of Ophthalmology* 43(2):134-146.

Lal, A. (1993). "Drop Volume of Commerical Anti-Glaucoma Eye Drops," *Indian Journal of Pharmacology* 25:163-164.

Pavan-Langston, D. (1996). *Manual of Ocular Diagnosis and Therapy*. Fourth Edition, Little, Brown and Company: New York, pp. 162-165.

\* cited by examiner

TRANSSCLERAL DELIVERY

RELATED APPLICATION

This application claims priority benefit of U.S. provisional application No. 60/503,840, filed Sep. 18, 2003, titled Transscleral Delivery, the contents of which is incorporated herein by reference in its entirety.

FIELD

Described herein are methods, compositions, and devices for the treatment of ocular diseases by the transscleral delivery of therapeutic agents, particularly the treatment of wet AMD by transscleral delivery of rapamycin.

BACKGROUND

The retina of the eye contains the cones and rods that detect light. In the center of the retina is the macula lutea, which is about ⅓ to ½ cm in diameter. The macula provides detailed vision, particularly in the center (the fovea), because the cones are higher in density. Blood vessels, ganglion cells, inner nuclear layer and cells, and the plexiform layers are all displaced to one side (rather than resting above the cones), thereby allowing light a more direct path to the cones.

Under the retina are the choroid, comprising a collection of blood vessels embedded within a fibrous tissue, and the deeply pigmented epithelium, which overlays the choroid layer. The choroidal blood vessels provide nutrition to the retina (particularly its visual cells).

There are a variety of retinal disorders for which there is currently no treatment or for which the current treatment is not optimal. Retinal disorders such as uveitis (an inflammation of the uveal tract: iris, ciliary body, and choroid), macular degeneration, macular edema, proliferative diabetic retinopathy, and retinal detachment generally are all retinal disorders that are difficult to treat with conventional therapies.

Age-related macular degeneration (AMD) is the major cause of severe visual loss in the United States for individuals over the age of 60. AMD occurs in either an atrophic or less commonly an exudative form. The atrophic form of AMD is also called "dry AMD," and the exudative form of AMD is also called "wet AMD."

In exudative AMD, blood vessels grow from the choriocapillaris through defects in Bruch's membrane, and in some cases the underlying retinal pigment epithelium. Organization of serous or hemorrhagic exudates escaping from these vessels results in fibrovascular scarring of the macular region with attendant degeneration of the neuroretina, detachment and tears of the retinal pigment epithelium, vitreous hemorrhage and permanent loss of central vision. This process is responsible for more than 80% of cases of significant visual loss in subjects with AMD. Currently there is no optimal treatment for wet AMD. Current or forthcoming treatments include laser photocoagulation, photodynamic therapy, treatment with pegylated aptamers, and treatment with certain small molecule agents.

Several studies have recently described the use of laser photocoagulation in the treatment of initial or recurrent neovascular lesions associated with AMD (Macular Photocoagulation Study Groups (1991) in *Arch. Ophthal.* 109:1220; *Arch. Ophthal.* 109:1232; *Arch. Ophthal.* 109:1242). Unfortunately, AMD subjects with subfoveal lesions subjected to laser treatment experienced a rather precipitous reduction in visual acuity (mean 3 lines) at 3 months follow-up. Moreover, at two years post-treatment treated eyes had only marginally better visual acuity than their untreated counterparts (means of 20/320 and 20/400, respectively). Another drawback of the procedure is that vision after surgery is immediately worse.

Photodynamic therapy (PDT) is a form of phototherapy, a term encompassing all treatments that use light to produce a beneficial reaction in a subject. Optimally, PDT destroys unwanted tissue while sparing normal tissue. Typically, a compound called a photosensitizer is administered to the subject. Usually, the photosensitizer alone has little or no effect on the subject. When light, often from a laser, is directed onto a tissue containing the photosensitizer, the photosensitizer is activated and begins destroying targeted tissue. Because the light provided to the subject is confined to a particularly targeted area, PDT can be used to selectively target abnormal tissue, thus sparing surrounding healthy tissue. PDT is currently used to treat retinal diseases such as AMD. PDT is currently the mainstay of treatment for subfoveal choroidal neovascularization in subjects with AMD (Photodynamic Therapy for Subfoveal Choroidal Neovascularization in Age Related Macular Degeneration with Verteporfin (TAP Study Group) *Arch Ophthalmol.* 1999 117:1329-1345.

Choroidal neovascularization (CNV) has proven recalcitrant to treatment in most cases. Conventional laser treatment can ablate CNV and help to preserve vision in selected cases not involving the center of the retina, but this is limited to only about 10% of the cases. Unfortunately, even with successful conventional laser photocoagulation, the neovascularization recurs in about 50-70% of eyes (50% over 3 years and >60% at 5 years). (Macular Photocoagulation Study Group, *Arch. Ophthalmol.* 204:694-701 (1986)). In addition, many subjects who develop CNV are not good candidates for laser therapy because the CNV is too large for laser treatment, or the location cannot be determined so that the physician cannot accurately aim the laser. Photodynamic therapy, although utilized in up to 50% of new cases of subfoveal CNV has only marginal benefits over natural history, and generally delays progression of visual loss rather than improving vision which is already decreased secondary to the subfoveal lesion. PDT is neither preventive or definitive. Several PDT treatments are usually required per subject and additionally, certain subtypes of CNV fare less well than others.

Although there is currently some off label use of intravitreal triamcinolone acetate, there are no other widely accepted therapies for subfoveal CNV. (Combined photodynamic Therapy with Verteporfin and Intravitreal Triamcinolone Acetonide for Choroidal Neovascularization. *Ophthalmol* 2003: 110:1517-1525).

Thus, there remains a long-felt need for methods, compositions, and devices that may be used to optimally prevent or significantly inhibit choroidal neovascularization and to prevent and treat wet AMD.

In addition to AMD, choroidal neovascularization is associated with such retinal disorders as presumed ocular histoplasmosis syndrome, myopic degeneration, angioid streaks, idiopathic central serous chorioretinopathy, inflammatory conditions of the retina and or choroid, and ocular trauma. Angiogenic damage associated with neovascularization occurs in a wide range of disorders including diabetic retinopathy, venous occlusions, sickle cell retinopathy, retinopathy of prematurity, retinal detachment, ocular ischemia and trauma.

Uveitis is another retinal disorder that has proven difficult to treat using existing therapies. Uveitis is a general term that indicates an inflammation of any component of the uveal tract. The uveal tract of the eye consists of the iris, ciliary body, and choroid. Inflammation of the overlying retina, called retinitis, or of the optic nerve, called optic neuritis, may occur with or without accompanying uveitis.

Uveitis is most commonly classified anatomically as anterior, intermediate, posterior, or diffuse. Posterior uveitis signifies any of a number of forms of retinitis, choroiditis, or optic neuritis. Diffuse uveitis implies inflammation involving all parts of the eye, including anterior, intermediate, and posterior structures.

The symptoms and signs of uveitis may be subtle, and vary considerably depending on the site and severity of the inflammation. Regarding posterior uveitis, the most common symptoms include the presence of floaters and decreased vision. Cells in the vitreous humor, white or yellow-white lesions in the retina and/or underlying choroid, exudative retinal detachments, retinal vasculitis, and optic nerve edema may also be present in a subject suffering from posterior uveitis.

Ocular complications of uveitis may produce profound and irreversible loss of vision, especially when unrecognized or treated improperly. The most frequent complications of posterior uveitis include retinal detachment; neovascularization of the retina, optic nerve, or iris; and cystoid macular edema.

Macular edema (ME) can occur if the swelling, leaking, and hard exudates noted in background diabetic retinopathy (BDR) occur within the macula, the central 5% of the retina most critical to vision. Background diabetic retinopathy (BDR) typically consists of retinal microaneurisms that result from changes in the retinal microcirculation. These microaneurisms are usually the earliest visible change in retinopathy seen on exam with an ophthalmoscope as scattered red spots in the retina where tiny, weakened blood vessels have ballooned out. The ocular findings in background diabetic retinopathy progress to cotton wool spots, intraretinal hemorrhages, leakage of fluid from the retinal capillaries, and retinal exudates. The increased vascular permeability is also related to elevated levels of local growth factors such as vascular endothelial growth factor. The macula is rich in cones, the nerve endings that detect color and upon which daytime vision depends. When increased retinal capillary permeability effects the macula, blurring occurs in the middle or just to the side of the central visual field, rather like looking through cellophane. Visual loss may progress over a period of months, and can be very annoying because of the inability to focus clearly. ME is a common cause of severe visual impairment.

As described above, treatment for CNV and other retinoproliferative conditions is primarily with laser photocoagulation. There have been many attempts, however, to treat these and other conditions such as macular edema and chronic inflammation with pharmaceuticals. For example, use of rapamycin to inhibit CNV and wet AMD has been described in U.S. application Ser. No. 10/665,203, which is incorporated herein by reference in its entirety. There are no approved medicines for CNV or proliferative retinopathy, but there is a great need for such a therapy, and the use of rapamycin to treat inflammatory diseases of the eye has been described in U.S. Pat. No. 5,387,589, titled Method of Treating Ocular Inflammation, with inventor Prassad Kulkarni, assigned to University of Louisville Research Foundation, the contents of which is incorporated herein in its entirety.

There are currently no approved devices to deliver therapeutic agents to the posterior segment of the eye from a location external to the eye. Likewise, except for steroid formulations, no therapeutic agents are delivered to the posterior segment from external injection sites with long acting delivery profiles. Particularly for chronic diseases, including those described herein, there is a great need for long acting methods for delivering active compounds to the posterior segment to treat CNV in such diseases as AMD, macular edema, proliferative retinopathies, and chronic inflammation.

Direct delivery of therapeutic agents to the eye as opposed to systemic administration is advantageous because the therapeutic agent concentration at the site of action is increased relative to the therapeutic agent concentration in a subject's circulatory system. Additionally, therapeutic agents are likely to have undesirable side effects when delivered systemically to treat posterior segment disease. Thus, localized drug delivery promotes efficacy while decreasing side effects and systemic toxicity.

Direct delivery can be achieved by placing the therapeutic agent directly into the interior of the eye, usually by injection, or can be achieved by delivering the therapeutic agent from a position external to the eye. One example of such external placement is delivery of a therapeutic agent by transscleral delivery. In transscleral delivery, a composition or device containing the therapeutic agent is placed outside of the sclera and the therapeutic agent diffuses across the sclera towards the interior of the eye. Direct placement of the therapeutic agent into the interior of the eye usually requires invasive placement procedures. In contrast, placement of the therapeutic agent external to the eye can be achieved much more easily. An additional advantage of external placement of a composition or device containing a therapeutic agent is that the device or composition is not present in the interior of the eye for extended periods of time. Interior placement, however, will result in a composition or device being present in the interior of the eye, which may have adverse effects on the proper functioning of the eye. For these reasons, external delivery is often to be preferred over direct delivery to the interior of the eye.

Although transscleral delivery of therapeutic agents to the eye is advantageous, there are many difficulties in developing such delivery mechanisms. The delivery system, whether it is a composition or device, will need to be of small size to enable placement of the composition or device in the ocular region close to the sclera. The delivery system will have to be large enough, however, to contain amounts of the therapeutic agent capable of delivering therapeutically effective amounts of the agent. If delivery of the therapeutic agent is needed for an extended period of time, the composition or device must be able to contain enough therapeutic agent to deliver therapeutic amounts for the extended period and must be able to remain in position for the extended period of time to allow extended delivery of the therapeutic agent. The delivery system may also need to minimize delivery to other tissues in the vicinity and concentrate delivery towards the interior of the eye.

SUMMARY

The methods, compositions, and devices described herein allow transscleral delivery of a therapeutic agent and address one or more of the difficulties described above. As such, the methods, compositions, and devices described herein can be used to deliver a variety of therapeutic agents for extended periods of time and can be used for the prevention and treatment of a number of diseases of the eye.

Described herein are methods, compositions and devices for the transscleral delivery of an amount of rapamycin effective to treat wet AMD in a human subject.

As described in further detail in the Detailed Description section, the methods, compositions and devices may also be used for the transscleral delivery of therapeutically effective amounts of rapamycin for the treatment, prevention, inhibition, delaying of the onset of, or causing the regression of wet AMD. The methods, compositions and devices may also be used for the transscleral delivery of therapeutically effective amounts of rapamycin for the treatment, prevention, inhibition, delaying of the onset of, or causing the regression of CNV. The methods, compositions and devices may also be used for the transscleral delivery of therapeutically effective amounts of rapamycin for the treatment, prevention, inhibition, delaying of the onset of, or causing the regression of angiogenesis in the eye. Other diseases and conditions that may be treated, prevented, inhibited, have onset delayed, or caused to regress using rapamycin are described in the Diseases and Conditions section of the Detailed Description.

As described in further detail in the Detailed Description, the methods, compositions and devices may also be used for the transscleral delivery of therapeutically effective amounts of therapeutic agents other than rapamycin for the treatment, prevention, inhibition, delaying of the onset of, or causing the regression of wet AMD. Therapeutic agents that may be used are described in detail in the Therapeutic Agents section. Such therapeutic agents include but are not limited to immunophilin binding compound. Immunophilin binding compound that may be used include but are not limited to the limus family of compounds, including rapamycin, SDZ-RAD, tacrolimus, everolimus, pimecrolimus, CCI-779, AP23841, ABT-578, and analogs, salts and esters thereof. The methods, compositions and devices may also be used for the transscleral delivery of therapeutically effective amounts of therapeutic agents for the treatment, prevention, inhibition, delaying of the onset of, or causing the regression of CNV. The methods, compositions and devices may also be used for the transscleral delivery of therapeutically effective amounts of therapeutic agents for the treatment, prevention, inhibition, delaying of the onset of, or causing the regression of angiogenesis in the eye. Other diseases and conditions that may be treated, prevented, inhibited, have onset delayed, or caused to regress using therapeutic agents other than rapamycin are described in the Diseases and Conditions section of the Detailed Description.

Described in the Detailed Description are various compositions, routes of administration, and delivery systems that may be used for delivering a therapeutically effective amount of rapamycin or other therapeutic agents for the treatment, prevention, inhibition, delaying of the onset of, or causing the regression of wet AMD, CNV, angiogenesis or other diseases or conditions of the eye. Compositions that may be used include but are not limited to a solid form of the therapeutic agent, a suspension of the therapeutic agent, a solution of the therapeutic agent, and incorporation of the therapeutic agent into a polymer formulation. Such polymer formulation may be a biodegradable polymer formulation or a non-biodegradable polymer formulation. Routes of administration and delivery systems that may be used include but are not limited to placement of the composition or device by injection, delivery by a solid polymer implant, delivery by a backed solid polymer implant, delivery by a solid bioadhesive implant, delivery by a solid implant with anchoring surface, delivery by solid implant with delayed release, delivery by coated suture, delivery by coiled fiber, and delivery using a solid therapeutic agent composition.

Described are various methods for the treatment, prevention, inhibition, delaying of the onset of, or causing the regression of wet AMD, CNV, angiogenesis or other diseases or conditions of the eye. In one method, the eye has a sclera with an outer scleral surface and the rapamycin or other therapeutic agent is administered transsclerally by placement of a delivery system proximate to the outer scleral surface.

In one such method, the delivery system contains a solid core of rapamycin or other therapeutic agent. This delivery system may also optionally contain a backing portion that is substantially impermeable to the rapamycin or other therapeutic agent.

In another method, the delivery system contains a suspension of particles of rapamycin or other therapeutic agent. These particles may generally be of any size. Described is one delivery system in which the particles of rapamycin or other therapeutic agent have an average diameter of less than about 50 µm. Other particles that may be used are described in the Detailed Description.

In another method, the delivery system contains a solution of rapamycin or other therapeutic agent. Such solution may generally contain any concentration of rapamycin or other therapeutic agent as limited by the solubility of the rapamycin or other therapeutic agent in the solvent. Various solvents and concentrations that may be used are described in the Detailed Description.

In another method, the delivery system comprises rapamycin or other therapeutic agent dispersed in a polymer implant. The implant may be a biodegradable polymer implant or may be a non-biodegradable polymer implant. Such implants may optionally include a backing that is substantially impermeable to rapamycin or other therapeutic agent.

The implants may generally be of any shape and size allowing for delivery of the required amounts of rapamycin or other therapeutic agent and placement proximate to the outer scleral surface. Various shapes and sizes of implant that may be used are described in the Detailed Description. As a nonlimiting example, the implant may be shaped as a disk. As another nonlimiting example, the polymer implant may be shaped as a suture, which may generally be of any dimensions including but not limited to a length of less than about 10 cm and a diameter of less than about 2 mm. As another nonlimiting example, the polymer implant may be shaped as a coiled fiber, which may generally be of any dimensions including but not limited to a length of less than about 5 cm and a diameter of less than about 1 mm.

As a nonlimiting example of the size of the implants that may be used, described herein is a polymer implant having a scleral surface portion for placement on the outer scleral surface of the eye and through which the rapamycin or other therapeutic agent is delivered to the outer scleral surface, and this scleral surface portion has an area of less than about 0.5 cm$^2$. Other sizes that may be used are described in the Detailed Description.

The polymer implant may also optionally include various means for assisting in anchoring the implant in place. As one nonlimiting example, such a polymer implant may include a bioadhesive layer for placement on the outer scleral surface of the eye. As another nonlimiting example, such a polymer implant may have a surface containing a number of protrusions which assist in anchoring the polymer implant to the outer scleral surface of the eye. As another nonlimiting example, such a polymer implant may be sutured to the sclera or other tissue.

The polymer implant may also optionally be a delayed release implant. As one nonlimiting example, such a polymer implant includes a rapamycin or other therapeutic agent containing portion that is coated with a coating that contains a concentration of rapamycin or other therapeutic agent that is less than the concentration of rapamycin therapeutic agent in the rapamycin therapeutic agent containing portion. In one nonlimiting example of such a delayed release implant, the therapeutic agent is rapamycin and the concentration of rapamycin in the coating is such that release of rapamycin from the coating does not deliver a wound healing inhibiting amount of rapamycin.

The implants and other delivery systems described herein may deliver the rapamycin or other therapeutic agent for an extended period of time. One nonlimiting example of such extended release delivery system is a delivery system that delivers rapamycin transsclerally in an amount sufficient to maintain an amount effective to treat wet age-related macular degeneration for an extended period of time. In one nonlimiting example, such a delivery system delivers the rapamycin transsclerally in an amount sufficient to treat wet age-related macular degeneration for at least about three weeks. Such a delivery system may generally be any delivery system described herein, and in one nonlimiting example the delivery system is a solid polymer implant. Other extended periods of release are described in the Detailed Description.

When the therapeutic agent is rapamycin, the implants and other delivery systems described herein may be used to maintain a concentration of rapamycin at the outer scleral surface. In one nonlimiting example, it is believed that a delivery system maintaining a concentration of rapamycin of about 2 µg/ml at the outer scleral surface may be used for treatment of wet AMD. Other concentrations that may be used are described in the Detailed Description.

When the therapeutic agent is rapamycin, the implants and other delivery systems described herein may be used to deliver a dose of rapamycin to the posterior segment of the eye. In one nonlimiting example, it is believed that a delivery system delivering about 1 µg of rapamycin per day may be used for the treatment of wet AMD. Other delivery doses that may be used are described in the Detailed Description.

DETAILED DESCRIPTION

Figure 1:
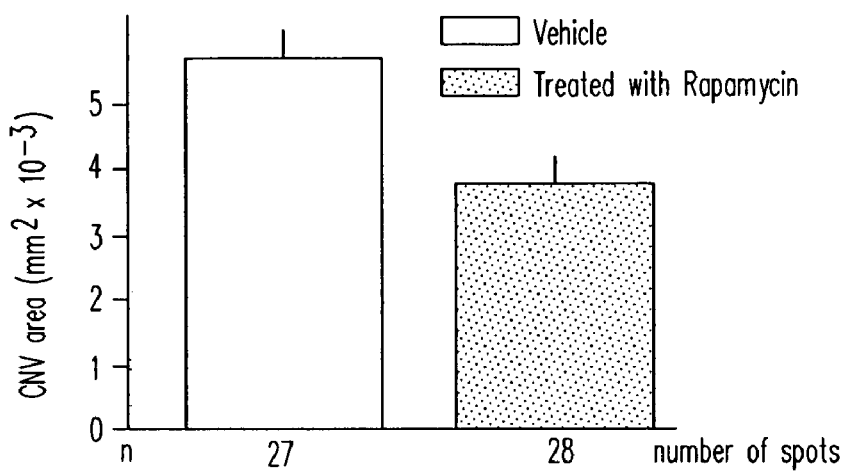
FIG. 1 depicts the efficacy of periocular injections of rapamycin for preventing choroidal neovascularization.

Described in this section are compositions, devices, and methods relating to the transscleral delivery of therapeutic agents to the eye, particularly to the posterior segment the eye, and particularly for delivery for an extended duration. These compositions, devices, and methods may be used for the treatment, prevention inhibition, delaying onset of, and causing regression of diseases and unwanted conditions of the posterior segment, including but not limited to choroidal neovascularization; macular degeneration; age-related macular degeneration, including wet AMD; retinal angiogenesis; chronic uveitis; and other retinoproliferative conditions.

In this detailed description section are described (1) the therapeutic agents that may be delivered transsclerally using the compositions, devices, and methods described herein, (2) the diseases and conditions that may be treated by transscleral delivery of the therapeutic agents, (3) the compositions, devices, and methods that may be used for transscleral delivery of the therapeutic agents, and (4) specific description of the treatment of CNV and wet AMD by transscleral delivery of rapamycin.

Therapeutic Agents

Most generally, any compounds and compositions currently known or yet to be discovered that are useful in treating, preventing, inhibiting, delaying the onset of, or causing the regression of the diseases and conditions described herein may be therapeutic agents for use in the compositions, devices, and methods described herein.

Therapeutic agents that may be used include compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories). Limus compound analogs and derivatives that may be used include but are not limited to the compounds described in U.S. Pat. Nos. 5,527,907; 6,376,517; and 6,329,386 and U.S. patent application Ser. No. 09/950,307, all of which are incorporated herein by reference in their entirety.

The limus family of compounds may be used in the compositions, devices and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

Other therapeutic agents that may be used include those disclosed in the following patents and publications, the contents of each of which is incorporated herein in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkarni, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; PCT publication WO 2004/028477, published Apr. 8, 2004, titled Method subretinal administration of therapeutics including steroids: method for localizing pharmadynamic action at the choroid and retinat; and related mathods for treatment and or prevention of retinal diseases, assigned to Innorx, Inc; U.S. Pat. No. 6,416,777, issued Jul. 9, 2002, titled Opthalmic drug delivery device, assigned to Alcon Universal Ltd; and U.S. Pat. No. 6,713,081, issued Mar. 30, 2004, titled Ocular therapeutic agent delivery device and methods for making and using such devices, assigned to Department of Health and Human Services.

Other therapeutic agents that may be used include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-v/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agents may also be used in combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-v/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

Diseases and Conditions that May be Treated

In this section are described diseases and conditions that may be treated or prevented using the therapeutic agents and the compositions, devices, and methods described herein.

Generally, any diseases or condition of the eye susceptible to treatment, prevention, inhibition, delaying the onset of, or causing the regression of using the therapeutic agents and the compositions, devices and methods described herein may be treated or prevented, including but not limited to diseases or conditions of the posterior segment of the eye. Such posterior segment diseases or conditions include, but are not limited to, diseases or conditions associated with neovascularization including retinal and/or choroidal neovascularization.

Diseases or conditions associated with retinal and/or choroidal neovascularization that can be treated, prevented inhibited, have onset delayed, or be caused to regress using the compositions, devices, and methods described herein include, but are not limited to, diabetic retinopathy, macular degeneration, retinopathy of prematurity (retrolental fibroplasia), infections causing a retinitis or choroiditis, presumed ocular histoplasmosis, myopic degeneration, angioid streaks, ocular trauma, and AMD. Other non-limiting examples of diseases and unwanted conditions that may be treated, prevented inhibited, have onset delayed, or be caused to regress using the compositions, devices, and methods described herein include, but are not limited to, pseudoxanthoma elasticum, vein occlusion, artery occlusion, carotid obstructive disease, Sickle Cell anemia, Eales disease, myopia, chronic retinal detachment, hyperviscosity syndromes, toxoplasmosis, trauma, polypoidal choroidal vasculopathy, post-laser complications, complications of idiopathic central serous chorioretinopathy, complications of choroidal inflammatory conditions, rubeosis, diseases associated with rubeosis (neovascularization of the angle), neovascular glaucoma, chronic uveitis, macular edema, proliferative retinopathies and diseases or conditions caused by the abnormal proliferation of fibrovascular or fibrous tissue, including all forms of proliferative vitreoretinopathy (including post-operative proliferative vitreoretinopathy), whether or not associated with diabetes.

One disease that may be treated, prevented inhibited, have onset delayed, or be caused to regress using the composition, devices and methods described herein is the wet form of AMD. The wet form of AMD is characterized by blood vessels growing from their normal location in the choroid into an undesirable position under the retina. Leakage and bleeding from these new blood vessels results in vision loss and possibly blindness.

The compositions, devices, and methods described herein may also be used to prevent or slow the transition from the dry form of AMD (wherein the retinal pigment epithelium or RPE degenerates and leads to photoreceptor cell death and the formation of yellow deposits called drusen under the retina) to the wet form of AMD.

"Macular degeneration" is characterized by the excessive buildup of fibrous deposits in the macula and retina and the atrophy of the retinal pigment epithelium. As used herein, an eye "afflicted" with macular degeneration is understood to mean that the eye exhibits at least one detectable physical characteristic associated with the disease of macular degeneration. The administration of rapamycin appears to limit excessive angiogenesis, such as choroidal neovascularization in age-related macular degeneration (AMD), which may occur without such treatment. As used herein, the term "angiogenesis" means the generation of new blood vessels ("neovascularization") into a tissue or organ. An "angiogenesis-mediated disease or condition" of the eye or retina is one in which new blood vessels are generated in a pathogenic manner in the eye or retina, resulting in loss of vision or other problem, e.g., choroidal neovascularization associated with AMD.

As used herein, to "inhibit" a disease or condition by administration of a therapeutic agent means that the progress of at least one detectable physical characteristic or symptom of the disease or condition is slowed or stopped following administration of the therapeutic agent as compared to the progress of the disease or condition without administration of the therapeutic agent.

As used herein, to "prevent" a disease or condition by administration of a therapeutic agent means that the detectable physical characteristics or symptom of the disease or condition do not develop following administration of the therapeutic agent.

As used herein, to "delay onset of" a disease or condition by administration of a therapeutic agent means that at least one detectable physical characteristic or symptom of the disease or condition develops later in time following administration of the therapeutic agent as compared to the progress of the disease or condition without administration of the therapeutic agent.

As used herein, to "treat" a disease or condition by administration of a therapeutic agent means that the progress of at least one detectable physical characteristic or symptom of the disease or condition is slowed, stopped, or reversed following administration of the therapeutic agent as compared to the progress of the disease or condition without administration of the therapeutic agent.

As used herein, to "cause regresssion of" a disease or condition by administration of a therapeutic agent means that the progress of at least one detectable physical characteristic or symptom of the disease or condition is reversed to some extent following administration of the therapeutic agent.

A subject having a predisposition for or in need of prevention may be identified by the skilled practitioner by established methods and criteria in the field. The skilled practitioner may also readily diagnose individuals as in need of inhibition or treatment based upon established criteria in the field for identifying unwanted angiogenesis and/or neovascularization.

As used herein, a "subject" is generally any animal that may benefit from administration of the therapeutic agents described herein. The therapeutic agents may be administered to a mammal subject. The therapeutic agents may be administered to a human subject. The therapeutic agents may be administered to a veterinary animal subject. The therapeutic agents may be administered to a model experimental animal subject.

Other diseases and conditions that may be treated, prevented, inhibited, have the onset delayed, or be caused to regress using the methods described herein include those disclosed in the following patents and publications, the contents of each of which is incorporated herein in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkarni, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; PCT publication WO 2004/028477, published Apr. 8, 2004, titled Method subretinal administration of therapeutics including steroids: method for localizing pharmadynamic action at the choroid and retinat; and related mathods for treatment and or prevention of retinal diseases, assigned to Innorx, Inc; U.S. Pat. No. 6,416,777, issued Jul. 9, 2002, titled Opthalmic drug delivery device, assigned to Alcon Universal Ltd; and U.S. Pat. No. 6,713,081, issued Mar. 30, 2004, titled Ocular therapeutic agent delivery device and methods for making and using such devices, assigned to Department of Health and Human Services.

Compositions, Devices, and Methods for Transscleral Delivery Of Therapeutic Agents In this section are described compositions, devices, and methods for the transscleral delivery of the therapeutic agents described in the Therapeutic Agents section. Delivery of therapeutic agents using the compositions, devices and methods described in this section may be used to treat, prevent, inhibit, delay the onset of, or cause the regression of the diseases and conditions described in the Diseases and Conditions section. The compositions and devices described herein are examples of "therapeutic agent delivery systems," that may be used for the transscleral delivery the therapeutic agents described in the Therapeutic Agents section. Other compositions and devices in addition to those explicitly described herein may be used as "therapeutic agent delivery systems." When the therapeutic agent delivered is rapamycin, the delivery systems are referred to as "rapamycin delivery systems."

In this section are first described how the compositions, devices, and methods may be used to deliver amounts of the therapeutic agents effective for treating, preventing, inhibiting, delaying on set of, or causing the regression of the diseases and conditions described in the Diseases and Conditions section, including a description of how the compositions, devices and methods may be used for extended release and delayed release of the therapeutic agents. Then described are compositions and delivery systems that may be used for transscleral delivery of therapeutically effective amounts of the therapeutic agents, and methods for placement of the compositions and devices.

An "effective amount," which is also referred to herein as a "therapeutically effective amount," of a therapeutic agent for administration as described herein is that amount of the therapeutic agent that provides the therapeutic effect sought when administered to the subject. The achieving of different therapeutic effects may require different effective amounts of therapeutic agent. For example, the therapeutically effective amount of a therapeutic agent used for preventing a disease or condition may be different from the therapeutically effective amount used for treating, inhibiting, delaying the onset of, or causing the regression of the disease or condition. In addition, the therapeutically effective amount may depend on the age, weight, and other health conditions of the subject as is well know to those versed in the disease or condition being addressed. Thus, the therapeutically effective amount may not be the same in every subject to which the therapeutic agent is administered.

An effective amount of a therapeutic agent for treating, preventing, inhibiting, delaying the onset of, or causing the regression of a specific disease or condition is also referred to herein as the amount of therapeutic agent effective to treat, prevent, inhibit, delay the onset of, or cause the regression of the disease or condition.

Transscleral Delivery of Therapeutically Effective Amounts of Therapeutic Agents The compositions, methods, and devices described in this section deliver one or more therapeutic agents to the eye transsclerally in an amount and for a duration effective to treat, prevent, inhibit, delay the onset of, or cause the regression of the diseases and conditions described in the Diseases and Conditions section. As a non-limiting example, the compositions, devices, and methods described in this section may be used to deliver rapamycin transsclerally in amounts and for a duration effective to treat, prevent, inhibit, delay the onset of, or cause the regression of CNV and wet AMD. The effective amounts and durations may be different for each of treating, preventing, inhibiting, delaying the onset of, or causing the regression of CNV and wet AMD.

To calculate the amount of a therapeutic agent that can be delivered transsclerally it is necessary to understand the transport of the therapeutic agent across the sclera. See for example, Transscleral drug delivery for posterior segment disease, D. Geroski and H. Edelhauser, *Advanced Drug Delivery Reviews,* 52 (2001) 37-48. The transport of the therapeutic agent may depend on the composition or devices used for delivery of the therapeutic agent. Once the flux of a therapeutic agent across the sclera from a given composition or device is understood, the amount of therapeutic agent needed to maintain a therapeutically effective level of agent for a certain duration can be calculated and the appropriate delivery composition or device and dosage amount identified.

As a non-limiting example of such procedure for identifying the appropriate dosage and composition or device, the following analysis has been performed for transscleral delivery of rapamycin for treatment of CNV or wet AMD. As described in Example 3 below, the permeability of human sclera to rapamycin was determined by in-vitro experiment using ex-vivo human scleral tissue to be of the order of $1 \times 10^{-5}$ cm/sec. The flux of rapamycin delivered transsclerally will depend on the permeability of the sclera to rapamycin and the difference in concentration of rapamycin inside and outside of the sclera. It is expected that a device maintaining a rapamycin concentration of about 2 µg/ml at the outer scleral surface can produce a flux of about 2.4 µg/cm²/day. A device maintaining a higher concentration at the outer scleral surface would be expected to produce a proportionally higher flux. It is believed that delivery of about 1 µg of rapamycin per day to the posterior segment may be a therapeutically effective dose to treat CNV and wet AMD. Higher doses than about 1 µg of rapamycin per day may be needed to treat CNV and wet AMD. Based on these observations and assumption, it is believed that a device maintaining a concentration of rapamycin of about 2 µg/ml over an area of about 0.4 cm² of the outer scleral surface of a human eye will deliver an amount of rapamycin that is therapeutically effective to treat CNV and wet AMD. If a different therapeutic amount of rapamycin is required the necessary amount can be delivered by altering either the concentration of rapamycin maintained at the outer scleral surface, the area over which the rapamycin concentration is maintained, or a combination of both of these factors.

It is believed that one device or composition that may be useful for carrying out the methods described herein is a device or composition maintaining a rapamycin concentration of about 4 µg/ml at the outer scleral surface. It is believed that other devices and compositions that may be useful for carrying out the methods described herein are devices or compositions that maintain a rapamycin concentration at the outer scleral surface of about 0.1 µg/ml or less, about 0.5 µg/ml or less, about 1 µg/ml or less, about 2 µg/ml or less, about 5 µg/ml or less, about 10 µg/ml or less, about 20 µg/ml or less, about 50 µg/ml or less, about 100 µg/ml or less, about 200 µg/ml or less, about 500 µg/ml or less, about 1000 µg/ml or less, about 5,000 µg/ml or less, and about 10,000 µg/ml or less.

It is believed that devices and compositions that may be used in the methods described herein are devices or compositions that deliver transsclerally to the posterior segment of the eye an amount of rapamycin of about 0.1 µg/day or less, about 0.5 µg/day or less, about 1 µg/day or less, about 2 µg/day or less, about 5 µg/day or less, about 10 µg/day or less, about 20 µg/day or less, about 50 µg/day or less, about 100 µg/day or less, and about 200 µg/day or less.

For other therapeutic agents and for other diseases and conditions, a similar analysis may be performed to identify the effective amounts, compositions, devices and methods that may be used to deliver therapeutically effective amounts of the therapeutic agent.

For treatment, prevention, inhibition, delaying the onset of, or causing the regression of certain diseases or conditions, it may be desirable to maintain delivery of a therapeutically effective amount of the therapeutic agent for an extended period of time. Depending on the disease or condition being treated, prevented, inhibited, having onset delayed, or being caused to regress this extended period of time may be up to 1 week, up to 2 weeks, up to 3 weeks, up to 1 month, up to 3 months, up to 6 months, up to 9 months, up to 1 year, up to 18 months, up to 2 years, up to 3 years, or up to 4 years. Generally, however, any extended period of delivery may be possible. A therapeutically effective amount of agent may be delivered for an extended period by a device or composition that maintains for the extended period a concentration of agent at the outer scleral surface sufficient to deliver a therapeutically effective amount of agent for the extended time. By way of example only, and in no way limiting, under the earlier assumptions regarding delivery of rapamycin for treatment, prevention, inhibition, delaying the onset of, or causing the regression of CNV and wet AMD, it is believed that a device maintaining a concentration of about 2 µg/ml over an area of about 0.4 cm² of the outer scleral surface of a human eye for up to 6 months will deliver a therapeutically effective amount of rapamycin for up to 6 months. These calculations are based on an assumed therapeutic dose of 1 µg/day for treatment of AMD or CNV. If delivery of a larger dose of rapamycin is required, this may be achieved by a variety of ways including but not limited to increasing the concentration of rapamycin at the outer scleral surface, increasing the area over which the concentration is maintained, or some combination of these factors.

Delivery of a therapeutically effective amount of the therapeutic agent for an extended period may be achieved using application of one composition or device or may be achieved by application of two or more doses of composition or by placement of two or more devices. If the compositions or devices are nonbiodegradable, the prior composition or devices will likely need to be removed before application of the next composition or device. As a non-limiting example of such multiple applications, maintenance of the therapeutic amount of rapamycin for 6 months for treatment of wet AMD may be achieve by application of one composition or device delivering a therapeutic amount for 6 months or by sequential application of two compositions or devices each delivering a therapeutic amount for 3 months. The optimal dosage regime will depend on the therapeutic amount of the therapeutic agent needing to be delivered, the period over which it need be delivered, and the size of the device needed to satisfy these requirements. If a device needed to deliver the necessary amounts for the extended period is too large to be feasibly placed for transscleral delivery, two smaller devices each delivering for half of the extended period may be used. Someone versed in such extended therapeutic agent delivery dosing will understand how to identify dosing regimes that may be used.

When using certain therapeutic agents or for the treatment, prevention, inhibition, delaying the onset of, or causing the regression of certain diseases, it may be desirable for delivery of the therapeutic agent not to commence immediately upon placement of the device or composition into the eye region, but for delivery to commence after some delay. For example, but in no way limiting, such delayed release may be useful where the therapeutic agent inhibits or delays wound healing and delayed release is desirable to allow healing of any wounds occurring upon placement of the device or composition. Depending on the therapeutic agent being delivered and/or the diseases and conditions being treated or prevented this period of delay before delivery of the therapeutic agent commences may be about 1 hour, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, or about 42 days. Other delay periods may be possible. Delayed release devices that may be used are described below and other delayed release devices that may be used are know to people versed in the technology.

Compositions that May be Used for Delivery of the Therapeutic Agent

Generally, the therapeutic agent may be formulated in any composition capable of transscleral delivery of a therapeutically effective amount of the therapeutic agent for the required delivery period. Compositions include but are not limited to solid forms of the therapeutic agent; particles of the therapeutic agent suspended in a liquid, gel, or solid; the therapeutic agent dissolved in a solution; and the therapeutic agent dissolved or dispersed in a polymer material.

Solid Form of Therapeutic Agent

One composition that may be used is a composition in which the therapeutic agent is present as a solid core. As used herein, a "solid core" means that the therapeutic agent is present in the form of a discrete solid substance. The solid may be amorphous or crystalline. The solid may be pure or substantially pure therapeutic agent or may be therapeutic agent diluted with same other solid material. The therapeutic agent solid core may have any suitable shape, such as a pellet, wafer, disk, rod, sphere, or film.

The therapeutic agent solid core may be combined with other compositions and components in a delivery system or may be used alone for delivering the therapeutic agent. In one delivery system that may be used in the methods described herein, a solid core of therapeutic agent is backed by a therapeutic agent impermeable backing such as Teflon™, Polyesters such as polyethylene terpthalate, Polypropylene, Polystyrene or High density polyethylene. The impermeable backing may be placed on the side of the therapeutic agent solid core facing away from the sclera. Such a backing would serve to block or reduce diffusion of the therapeutic agent in the direction opposite from the desired diffusion direction through the sclera. In one delivery system that may be used in the methods described herein, a solid core of the therapeutic agent such as rapamycin is placed proximate to the outer scleral surface and a backing is placed on top of the solid core, causing preferential delivery of the therapeutic agent into the sclera. The solid core and backing may be placed separately or may be combined into a delivery system outside of the subject and placed together as a monolithic delivery system. The backing may be attached to the solid core using any methods known to those versed in such technologies. In one non-limiting example, a solid core containing rapamycin and coated on one side with a rapamycin impermeable substance has release lifetime on the order of years. Such a solid core delivery system may have an extended release period in excess of a year. Another device than may be used contains a biodegradable polymer backing that is not completely impermeable to the therapeutic agent but has such disparity of diffusion that for practical purposes the vast majority of the drug elutes toward the scleral surface. Generally, the backing may be made of any material that results in diminished diffusion of the therapeutic agent into the tissues proximate to the sclera as compared to diffusion into such tissues in the absence of the backing.

Suspension of Therapeutic Agent

One composition that may be used is a composition in which solid particles of the therapeutic agent are suspended in a suspending medium.

As a non-limiting example, particles of water insoluble therapeutic agents can be suspended in an aqueous medium. The therapeutic agent particles may be crystalline or amorphous. The particles may be stabilized with an acceptable polymeric surfactant including but not limited to Pluronics F108, F127, and F68, and Tetronics. In addition, a viscous polymer may be added to the suspension, assisting the localization in the sclera and ease of placement and handling. In some uses of the suspension composition, a pocket in the sclera may be surgically formed to receive an injection of the suspension. The hydrogel structure of the sclera can act as a rate-controlling membrane. Particles of solid therapeutic agent substance for forming a suspension can be produced by known methods including but not limited to via ball milling, for example by using ceramic beads. For example, a Cole Parmer ball mill such as Labmill 8000 may be used with 0.8 mm YTZ ceramic beads available from Tosoh or Norstone Inc.

As used herein, a "particle" refers to a solid substance having a diameter less than 500 µm and may be amorphous or crystalline and may be a pure substance or a mixture. As used herein, "suspension" refers to particles within a liquid medium wherein the particles do not substantially settle within the liquid medium during the period necessary to administer the suspension as described herein. In some embodiments, a "suspension" refers to a colloid. In other embodiments, a "suspension" refers to a mixture that is not a colloid.

One composition that may be used in the methods described herein is a suspension of particles of rapamycin having a mean particle size less than 5 µm in water or an aqueous cocktail suitable for injection into or proximate to the sclera. Upon injection, these rapamycin particles are imbedded in or proximate to the sclera, providing a sustained release of rapamycin. A scleral injection of 1 µL of a 9% suspension of rapamycin can be expected to provide delivery of rapamycin at a rate of approximately 1 µg/day for 90 days. This conclusion results from a flux of 2.4 µg/cm$^2$/day calculated from flux=DS/L, where D is the diffusion coefficient, assumed to be $2.2 \times 10^{-5}$ (MW)$^{-1/2}$ cm$^2$/s, S is aqueous solubility, assumed to be 1 µg/cm$^3$, L is the scleral thickness, assumed to be 0.05 cm, and MW is the molecular weight of rapamycin, which is 914 g/mol. Another composition that may be used is a suspension of particles of rapamycin having diameters in the range of about 10 µm to about 100 µm. Such a composition is expected to provide a longer release time of rapamycin.

Another composition that may be used is a suspension of particles of rapamycin having a mean particle size less than about 50 µm in water or an aqueous cocktail suitable for injection into or proximate to the sclera.

Solution of Therapeutic Agent

One composition that may be used is a composition in which the therapeutic agent is dissolved in a solvent. Generally, any solvent may be used in which the therapeutic agent dissolves and which can be administered to the subject. Generally, any concentration of therapeutic agent in solution can be used. The solution can be a saturated or supersaturated solution, and the solution can be a solution in contact with the therapeutic agent in solid form. The solvent may be a pure solvent or may be a mixture of liquid solvent components. The solution formed may be a gelling solution. Solvents and types of solutions that may be used are well know to those versed in such drug delivery technologies. See for example, Remington: The Science and Practice of Pharmacy, Twentieth Edition, Lippincott Williams & Wilkins; 20th edition (Dec. 15, 2000).

When the therapeutic agent is rapamycin, suitable solvents include but are not limited to DMSO, ethanol, and methanol. For rapamycin, other solvents that may be used include but are not limited to castor oil, propylene glycol, glycerine, polysorbate 80, benzyl alcohol, Dimethyl acetamide (DMA), dimethyl formamide (DMF), glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol 400, and polyglycolated capryl glyceride (Labrasol, Gattefosse).

Other methods that may be used to solubilize rapamycin are described in solubilization of rapamycin, P. Simamora et al. *Int'l J. Pharma* 213 (2001) 25-29, the contents of which is incorporated herein in its entirety.

As a nonlimiting example, rapamycin can be dissolved in 5% DMSO or methanol in a balanced salt solution. The rapamycin solution can generally contain any concentration of rapamycin. The rapamycin solution can be a saturated or supersaturated solution of rapamycin. The rapamycin solution can be in contact with solid rapamycin. In one nonlimiting example, rapamycin can be dissolved in a concentration of up to about 400 mg/ml.

Polymer Formulation of Therapeutic Agent

One composition that may be used is a composition in which the therapeutic agent is dispersed or dissolved in a polymer formulation. The polymer formulation may be a biodegradable polymer or a nonbiodegradable polymer. As used herein, a "biodegradable polymer," is a polymer that over time completely or partially loses its substantial form when placed in the body of a subject. Biodegradable polymers may lose their substantial form by a variety of means including but not limited to by erosion or dissolution of the polymer in the subject biofluids, or by cleavage of the polymer molecules, including but not limited to enzymatic cleavage and cleavage by hydrolysis. As is well known to those versed in the technology, the biodegradable polymer may lose its substantial form over an extended period of time depending on a variety of factors, including but not limited to the chemical composition of the polymer, the molecular weight of the polymer, the morphology of the polymer, the mechanism of dissolution or degradation, and the environment in which the polymer is placed. Unless the context makes clear otherwise, the terms "erodible polymer," "bioerodible polymer," "bioresorbable," or "bioabsorbable polymers" are used to mean the same as a "biodegradable polymer," as defined above. See, for example, the following articles, the contents of each of which is incorporated herein in its entirety: Biodegradable Polymers for the Controlled Release of Ocular Drugs, A Merkeli et. al, *Prog. Polym. Sci. Vol* 23, 563-580, 1998; *High Performance Biomaterials, A Comprehensive guide to medical and pharmaceutical applications*, edited by Michael Szycher,. Technomic Publishing Co, Inc. Lancaster—Basel—1991; Biodegradable Polymers in Controlled Drug Delivery, *CRC Critical Reviews in Therapeutic Drug Carrier Systems*, Vol. 1, CRC Press, Boca Raton, Fla. (1987); Kohn J, and Langer R, Bioresorbable and Bioerodible Materials, in *Biomaterials Science: An Introduction to Materials in Medicine*, Ratner B D, Hoffman A S, Schoen F J, and Lemons J E (eds), New York, Academic Press, pp 64-72, 1996; and Robinson J R, and Lee V H L (eds), *Controlled Drug Delivery: Fundamentals and Applications* (2nd ed), New York, Marcel Dekker, 1987.

Non-limiting examples of polymers for use as described herein include polyesters of molecular weight from about 4,000 to about 100,000, homopolymers and copolymers of polylactic acid and polyglycolic acid, polycaprolactone, homopolymers and copolymeres of polyanhydrides such as terephthalic acid anhydride, bis(p-anhydride) and poly(p-carboxyphenoxy) alkyl, homopolymers and copolymers of dicarboxylic acids such as sebacic, adipic, oxalic, phthalic and maleic acid, polymeric fatty acid dimer compounds such as polydodecanedioic acid polyorthoesters, poly(alkyl-2-cyanoacrylate) such as poly(hexyl-2-cyanoacrylate), collagen (gelatin), polyacetals, divinyloxyalkylenes, polydihydropyrans, polyphosphazenes, homopolymers and copolymers of amino acids such as copolymers of leucine and methyl glutamate, polydioxinones, polyalkylcyano acetates, polysaccharides and their derivatives such as dextran and cyclodextran, cellulose and hydroxymethyl cellulose.

Other polymers that may be used are well known to those versed in such polymer compositions and then uses for delivery of therapeutic agents, including but not limited to polymers described in Biodegradable Polymers for the Controlled Release of Ocular Drugs, A Merkeli et. al, *Prog. Polym. Sci.* Vol 23, 563-580, 1998; *High Performance Biomaterials, A Comprehensive guide to medical and pharmaceutical applications*, edited by Michael Szycher,. Technomic Publishing Co, Inc. Lancaster—Basel—1991; Biodegradable Polymers in Controlled Drug Delivery, *CRC Critical Reviews in Therapeutic Drug Carrier Systems*, Vol. 1, CRC Press, Boca Raton, Fla. (1987); Kohn J, and Langer R, Bioresorbable and Bioerodible Materials, in *Biomaterials Science: An Introduction to Materials in Medicine*, Ratner B D, Hoffman A S, Schoen F J, and Lemons J E (eds), New York, Academic Press, pp 64-72, 1996; and Robinson J R, and Lee V H L (eds), *Controlled Drug Delivery: Fundamentals and Applications* (2nd ed), New York, Marcel Dekker, 1987.

The therapeutic agent may be combined with the polymer to form the polymer formulation using standard methods well-known to those versed in such technology. The polymer formulation may contain other components in addition to the therapeutic agent and polymer as is well-known to those versed in such technology.

Additional Excipients and Adjuvants

The therapeutic agents for use as described herein, such as rapamycin, may be subjected to conventional pharmaceutical operations, such as sterilization and compositions containing the therapeutic agent may also contain conventional adjuvants, such as preservatives, stabilizers, wetting agents, emulsifiers, buffers etc. The therapeutic agents may also be formulated with pharmaceutically acceptable excipients for clinical use to produce a pharmaceutical composition. Formulations suitable for ocular administration may be presented as a solution, suspension, particles of solid material, a discrete mass of solid material, incorporated within a polymer matrix, or in any other form suitable for ocular administration. The therapeutic agents may be used to prepare a medicament for the treatment of any of the conditions described herein.

A composition containing a therapeutic agent such as rapamycin may contain one or more adjuvants appropriate for the indicated route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solution formulation is required the therapeutic agent may be dissolved in a substance including but not limited to polyethylene glycol, propylene glycol, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods, compositions and devices described herein. The carrier or diluent may include time delay material, such as glyceryl monostearate or glyceryl distearate alone or with a wax, or other materials well known in the art. The formulations for use as described herein may also include gel formulations, erodible and non-erodible polymers, micropsheres, and liposomes.

Other adjuvants and excipients that may be used include but are not limited to $C_8$-$C_{10}$ fatty acid esters such as softigen 767, polysorbate 80, Pluronics, Tetronics, Miglyol, and Transcutol.

The formulations may conveniently be presented in unit dosage form and may be prepared by conventional pharmaceutical techniques. Such techniques include the step of bringing into association the therapeutic agent and the pharmaceutical carrier(s) or excipient(s). The formulations may be prepared by uniformly and intimately bringing into associate the active ingredient with liquid carriers or finely divided solid carriers or both, and then, if necessary, shaping the product.

Delivery Systems and Routes of Administration that May be Used for Delivery of the Therapeutic Agent Generally the therapeutic agent and compositions containing the therapeutic agent may be delivered using any delivery system capable of transscleral delivery of a therapeutically effective amount of the therapeutic agent. Delivery systems and routes of administration that may be used include but are not limited to delivery by injection, solid polymer implant, backed solid polymer implant, solid bioadhesive implant; solid implant with anchoring surface, coated suture, coiled fiber, and solid therapeutic agent.

Delivery by Injection

One method that may be used to deliver the compositions and devices described herein is delivery by injection. In this method compositions and devices may be placed in various positions within the ocular region for transscleral delivery. Positions in which the compositions and devices may be placed include but are not limited to subconjunctival placement, subtenon placement and intrascleral placement. Methods that may be used for placement of the compositions and devices include but are not limited to subconjunctival injection, posterior subtenon injection, injection through a specially designed curved cannula for placement directly against the posterior sclera, injection into the sclera by a specially designed device or simple syringe, placement into the sclera by a specially designed inserter or injector, and placement against the scleral surface by a specially designed injector or inserter.

In one method that may be used, the therapeutic agent is dissolved in an appropriate solvent or solvent mixture and then injected into or proximate to the sclera according to any of the procedures mentioned above. In one method that may be used, the therapeutic agent is rapamycin and is dissolved in a suitable solvent, such as DMSO, ethanol, or methanol.

One composition that may be delivered by injection is a suspension of the therapeutic agent in hyaluronic acid that then dissolves leaving pure therapeutic agent proximate to the sclera.

Delivery by Solid Polymer Implant

One delivery system that may be used to deliver the composition is a delivery system in which the composition is delivered by placement of a solid polymer implant in the ocular region.

The solid polymer implant may be placed in the ocular region for transscleral delivery by a variety of means including but not limited to placement inside a surgically formed scleral flap, and placement proximate to the outer scleral surface. Positions in which the solid polymer implant may be placed include but are not limited to subconjunctival placement, subtenon placement, and intrascleral placement.

For placement in a scleral flap, either in the clinic, procedure room, or operating room the eye may be prepared in a standard preoperative manner, the sclera will be exposed, and the creation of the flap will be performed with an appropriate blade. A suture may or may not be required. For placement proximate to the outer scleral surface, either in the clinic, procedure room, or operating room the eye may be prepared in a standard preoperative manner, the sclera will be exposed, and the solid polymer implant placed into position.

In one device that may be used in the methods described herein, the therapeutic agent containing compositions are transsclerally delivered from a polymer implant containing the therapeutic agent. Such implants may enable controlled and prolonged release of the therapeutic agent from the polymer implant. Polymers that may be used are described in the Polymer Formulation section herein. As used herein, "implant" refers to a three-dimensional object that may or may not be deformable but that generally will maintain its shape in the absence of an external force. The polymer implant may be biodegradable or bioerodible such that the therapeutic agent is released as the polymer erodes or otherwise degrades. The polymer implant may also be non-biodegradable, for example, the implant may be made of silicone, and may be removed after delivery of the incorporated therapeutic agent. In this way, the polymer implant may be re-loaded with the therapeutic agent substance and reimplanted into the eye. In another polymer implant that may be used, the polymer is an in situ forming polymeric gel such that the polymer formulation is initially in a liquid form and transforms to a gel phase upon exposure to physiological conditions. A non-limiting example of such a polymer is Pluronic F-127. In another polymer implant that may be used, a bioadhesive compound, such as a fibrin glue, is used to form the therapeutic agent containing polymer implant. In another polymer implant that may be used, the therapeutic agent is combined with, or in, microspheres or nanoparticles to increase the duration of the therapeutic agent's release. In such polymer implants, the duration of therapeutic agent elution from the polymer may be between about 1 week and about 12 months. In another such polymer implant, the duration of elution is on the order of years.

In another polymer implant that may be used, the polymer implant with therapeutic agent incorporated is sutured into the desired position on the eye. For example, the implant can be sutured against the surface of the sclera.

The shape of the polymer implant can be any suitable shape such as, for example, a coil, a disk, an elliptical or circular disk, thin film, or rod. In one polymer implant that may be used, the polymer implant is in the shape of a coil which is designed such that once passed into the tissue of choice, the tail of the suture coils to increase the length of the suture that remains apposed to a tissue of choice, such as the sclera. In one polymer implant that may be used, the polymer implant is shaped as a rod such that it tapers into a filament that can be used to secure the rod to the tissue of choice.

Other polymer implants that may be used include but are not limited to devices such as a hydrogel or pluronic gel for placement against the eye, devices that can unfold and or unroll when placed against the eye wall to deliver a therapeutic agent.

Delivery by Backed Solid Polymer Implant

One delivery system that may be used to deliver the composition is a delivery system in which the composition is delivered by placement of a solid polymer implant that includes a backing. In such backed polymer implants, the polymer implants are designed to promote diffusion in a direction of choice.

One backed polymer implant that may be used includes an erodible polymer implant, such as a disk, cylinder, fiber, or film contains the active therapeutic agent, and a backing made of an erodible polymer that contains no therapeutic agent. The choice of the second erodible polymer can be such that elution of therapeutic agent from the implant in the direction of the second polymer is blocked or slowed, allowing for the therapeutic agent to be delivered primarily in one direction. In one version, the second polymer is substantially impermeable to the therapeutic agent. In another version, a non-erodible polymer may be used as the blocking polymer and removed at the conclusion of therapeutic agent delivery. As used herein, "substantially impermeable" is understood to mean that no amount of therapeutic agent or a clinically insignificant amount of therapeutic agent passes through the substantially impermeable barrier. In one version of such a device, a suture is sandwiched between the two different polymers to allow the structure to remain securely affixed to the sclera via the suture.

Generally, the backing can be made of any material that diminished diffusion of the therapeutic agent into the tissues proximate to the sclera as compared to diffusion into such tissues in the absence of the backing. The backing may be made of a biodegradable material or may be made of a non-biodegradable material. The backing material may be impermeable or substantially impermeable to the therapeutic agent or may be semi-permeable or permeable to the therapeutic agent. In one backed polymer implant, the material of the therapeutic agent containing polymer and the backing are the same, and the concentration of the therapeutic agent in the therapeutic agent containing polymer is greater than the concentration in the backing. In one such implant, the backing initially contains substantially no therapeutic agent.

Figure 5:
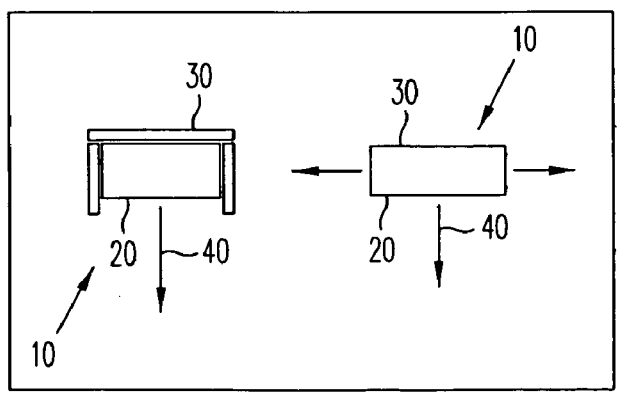
FIG. 5 depicts one delivery system that may be used in the methods described herein.

One version of such a delivery system is shown in FIG. 5, which shows a cross section of two version of a backed polymer implant (10), containing a therapeutic agent containing polymer component (20) and a backing (30). Such implants result in a preferential diffusion direction for the therapeutic agent (40).

Delivery by Solid Bioadhesive Implant

One delivery system that may be used to deliver the composition is a delivery system in which the composition is delivered by placement of a solid polymer implant that includes a bioadhesive surface.

The bioadhesive surface of the polymer implant allows the implant to be secured in place by adhesion to a biomaterial in the ocular region, including but not limited to adhesion to the outer scleral surface. The bioadhesive implant may be made of a bioadhesive polymer material or may be made of a non-bioadhesive polymer material that is coated with a bioadhesive material to form the bioadhesive surface. The preparation of drug delivery systems with bioadhesive surfaces is well known to those versed in the technology. See, for example, Bioadhesive any phase-change polymers for ocular drug delivery, J. Robinson et al., *Advanced Drug Delivery Review*, 16 (1995) 45-50, the contents of which is incorporated herein in its entirety.

Bioadhesive polymers that may be used include but are not limited to the following or any mixtures of the following: Polyvinyl pyrrolidone of various molecular weight, polyacrylic acid and copolymers of acrylic acid and acrylate esters, cross-linked polyacrylic acids (carbopols), celluloses (ethyl cellulose, methyl cellulose, microcrystalline cellulose, etc.,), cellulose derivatives (hydroxy ethyl cellulose, hydroxy propyl cellulose, hydroxypropyl methyl cellulose, carboxy methyl cellulose, etc.,), cellulose esters (cellulose acetate, cellulose phthalate, cellulose acetate phthalate, cellulose acetate butyrate, cellulose acetate propionate, etc.,), gums (gum arabica, tragacanth, gum acacia, gallen gum, xanthan gum, etc.,), hyaluronic acid and its derivatives, polyethylene oxides (polyox and derivatives, polyethylene glycol, and graft polymers of polyethylene oxides), chitosan and alginic acid.

The bioadhesive polymers may be mixed with suitable plasticizers to obtain a flexible film. Plasticizers that may be used include but are not limited to Propylene glycol, polypropylene glycol, polyethylene glycol, glycerol, glycerol esters (eg. glycerol monololeate), and esters of propylene glycol (eg. propylene glycol monolaurate), and water.

The bioadhesive polymers may be mixed with suitable wetting agents at a very low concentrations to improve surface contact when a bioadhesive implant is placed on the tissue: Wetting agents that may be used include but are not limited Surfactants: Cholesterol, tweens and spans, polysorbate 80, and pluronics.

The bioadhesive polymers may be mixed with suitable excipients, including but not limited to quickly dissolving water absorbent sugars/starches, such as mannitol, dextrose, lactose, maltodextrins. It is believed that because the tissues to which the implant will adhere possesses a certain amount of moisture, these sugars/starches will help absorb the moisture more quickly so that initial bioadhesion and contact is achieved more readily.

Delivery by Solid Implant with Anchoring Surface

One delivery system that may be used to deliver the composition is a delivery system in which the composition is delivered by placement of a solid polymer implant that includes an anchoring surface. In this drug delivery system, the polymer implant has a surface that has a morphology such that the implant is substantially immobilized by anchoring of the surface to a biomaterial in the ocular region, including but not limited to anchoring to the outer scleral surface of the eye.

Figure 15:
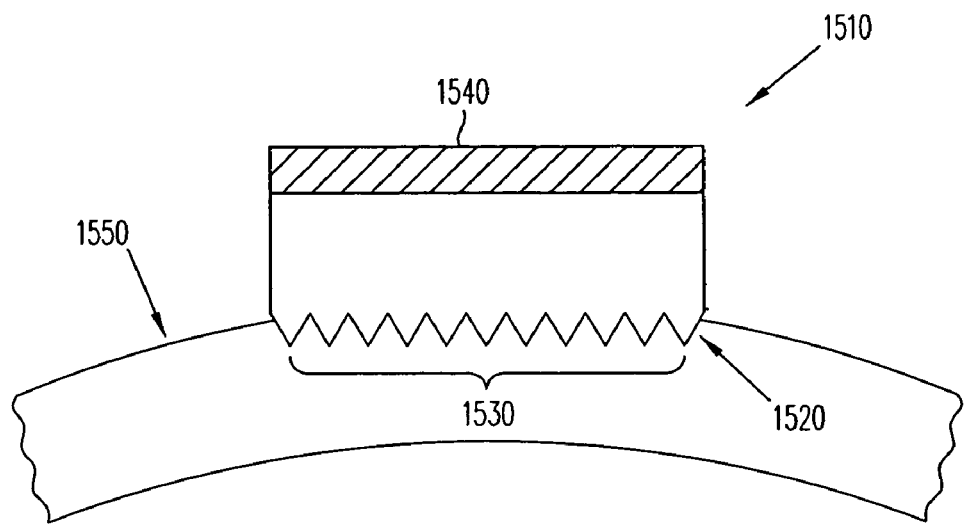
FIG. 15 depicts one delivery system that may be used in the methods described herein.

Non limiting examples of surfaces with a morphology capable of anchoring to a biomaterial include a surface containing a number of protrusions. An example of such a implant is shown in FIG. 15, depicting a polymer implant (1510) with an anchoring surface (1520) including a number of protrusions (1550), attaching the implant to the outer scleral surface (1530). The implant is depicted with an impermeable backing (1540), which is optional and may be omitted. The number, size, and geometry of the protrusions will depend on the nature of the material of which the protrusions are made and the surface to which they will be anchored. One versed in such technology will be able to identify the number, size, and geometry of protrusions that may be used.

Various anchoring surfaces are described. For example, the protrusions could be biodegradable or could be nonbiodegradable. In addition, the protrusions could contain therapeutic agent or could be substantially free of therapeutic agent. The protrusions may also be made of a material, and be of a size and shape that the anchoring surface of the implant perforates the outer scleral surface upon placement and this perforation enhances transport of the therapeutic agent across the sclera. In one example, the anchoring surface is made of a bioadhesive material. In another example, the anchoring surface is relatively hard when not in contact with bodily fluids, but softens and becomes more bioadhesive when placed in contact with bodily fluids. In this way, the relatively hard anchoring surface may be used to perforate the outer scleral surface upon placement of the implant, and subsequent to placement the anchoring surface becomes more bioadhesive adding to the ability of the surface to anchor the implant in place.

Figure 16A:
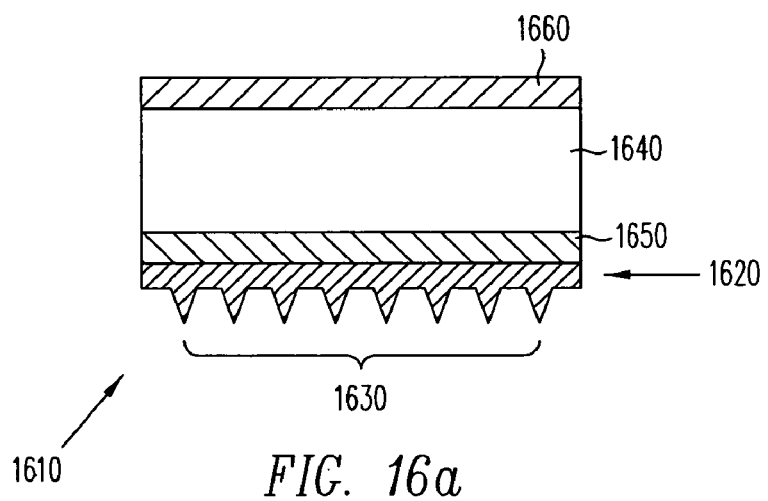
FIG. 16 depicts one delivery system that may be used in the methods described herein.
Figure 16B:
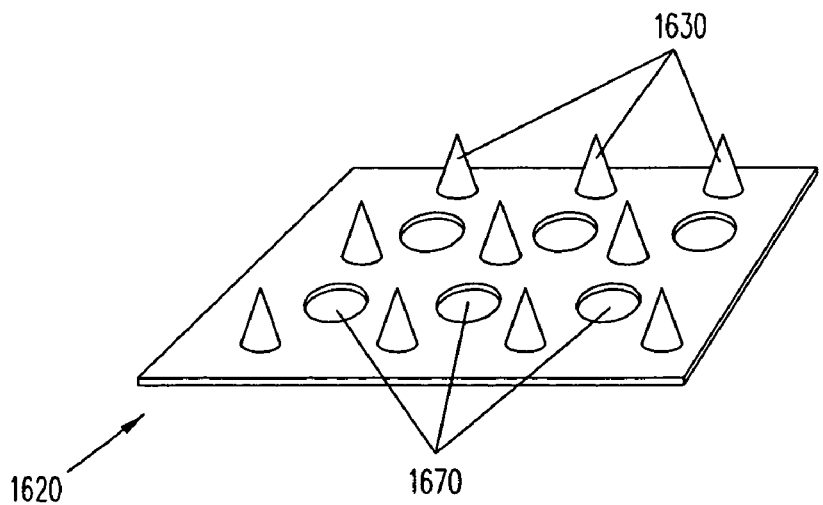

Another example of an implant with an anchoring surface is shown in FIG. 16, depicting a polymer implant (1610) with an anchoring surface (1620) including a number of protrusions (1630), with a portion of polymer containing the therapeutic agent (1640), a bioadhesive portion (1650), which may or may not contain therapeutic agent, and an impermeable backing (1660). The bioadhesive portion and the impermeable backing are optional and may be omitted. The portion containing the therapeutic agent (1640) may be bioadhesive. In this example, the anchoring surface (1620) contains protrusions (1630) and a number of holes (1670) through which the therapeutic agent may diffuse. Various geometries of the holes and protrusions will be feasible. In this example, the material from which the anchoring surface is made does not need to be permeable to the therapeutic agent, and the anchoring surface could be made of any suitable materials, including, for example, a metal. If a bioadhesive portion (1650) is present, the bioadhesive material may also move through the holes assisting in attachment of the implant to the outer scleral surface.

When the polymer implant includes a backing layer, this layer may generally be any backing as described in the Polymer implant with backing section. One implant that may be used includes a polyester or other non-biodegradable backing. Implants that may be used include but are not limited to a multi-layered system made of an active layer, containing the therapeutic agent; a nonactive, backing layer; a bioadhesive layer, which may or may not contain therapeutic agent, and an anchoring surface which may or may not contain therapeutic agent and may or may not be made of a bioadhesive material. Such a system may be produced in a variety of ways as is known to those versed in the technology, including but not limited to laminating the various layers together. In one polymer implant that may be used, the anchoring surface is the outer surface of the implant for attaching to the outer scleral surface. In another polymer implant that may be used, the anchoring surface is embedded in the laminate structure of the implant.

The polymer implant with anchoring surface may be placed in the same positions in the ocular region as the polymer implant may be placed.

Delivery by Solid Implant with Delayed Release

One delivery system that may be used to deliver the composition is a delivery system in which the composition is delivered by placement of a delayed release solid polymer implant.

In one delivery system, a polymer implant is designed such that the onset of therapeutic agent release is delayed for a period of time after polymer insertion into the eye. This delay allows for example, for time for the wound caused by the insertion of the implant to heal prior to therapeutic agent delivery. Such a delay is advantageous when the therapeutic agent itself inhibits wound healing. For example, therapeutic agents that inhibit fibroblastic proliferation, such as rapamycin, will inhibit wound healing. In one such delayed release implant that may be used, therapeutic agent release is delayed by coating the polymer implant containing the therapeutic agent with a polymer that contains no therapeutic agent but that will erode during a predetermined time. Thus, therapeutic agent release is delayed until a substantial portion of the polymer coating has eroded away. As used herein, a "substantial portion" of a substance refers to in excess of 80% of the substance. The polymer coating may be substantially impermeable to the therapeutic agent.

One versed in delayed release technology will be able to identify other compositions and devices that may be used to achieve the delayed release described herein.

Figure 6:
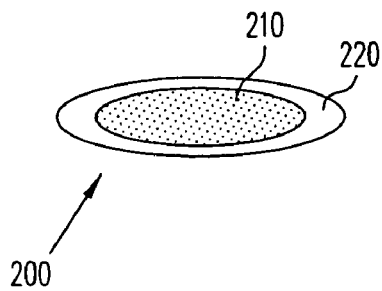
FIG. 6 depicts one delayed release delivery system that may be used in the methods described herein.

FIG. 6 shows one version of such a delivery system showing a cross-section of a delayed release delivery system (200), including a therapeutic agent containing polymer component (210), and a delayed release coating (220) that contains no or substantially no therapeutic agent.

The delayed release delivery system may be placed in the same positions in the ocular region in which the polymer implant may be placed.

Delivery by Coated Suture

One delivery system that may be used to deliver the composition is a delivery system in which the composition is delivered by placement of a solid coated suture. In one version of this delivery system, one or more therapeutic agents are incorporated into a suture, which can then be coated with the same or different therapeutic agent(s). For example, a therapeutic agent coating on the suture or other structure can be used to define a loading dose of the therapeutic agent to be delivered or include an anti-infective therapeutic agent.

Delivery by Coiled Fiber

One delivery system that may be used to deliver the composition is a delivery system in which the composition is delivered by placement of a coiled fiber containing the therapeutic agent. The coiled fiber may generally have any geometry and size to allow incorporation of sufficient therapeutic agent and allowing placement of the coiled fiber for transscleral delivery. One coiled fiber that may be used has a length of less than about 5 cm and a diameter of less than about 1 mm. Another coiled fiber that may be used has a length of less than about 10 cm and a diameter of less than about 2 mm. Other sizes may also be possible. The therapeutic agent may be incorporated into the body of the coiled fiber and be delivered transsclerally upon elution from the coiled fiber or upon erosion or degradation of the coiled fiber if the fiber is biodegradable. The therapeutic agent may also be incorporated on the surface of the coiled fiber. The coiled fiber may be placed in the same positions in the ocular region in which the polymer implant may be placed.

Delivery by Solid Therapeutic Agent

One delivery system that may be used to deliver the composition is a delivery system in which the composition is delivered by placement of a solid therapeutic agent.

The use of a composition with a solid therapeutic agent core is described in detail in the compositions section. Such a delivery system may be placed in the same position on the ocular region at which the polymer implant may be placed.

Examples of Delivery Systems

Depicted in FIGS. 7 to 14 are various nonlimiting examples of delivery systems that may be used in the methods described herein.

Figure 7:
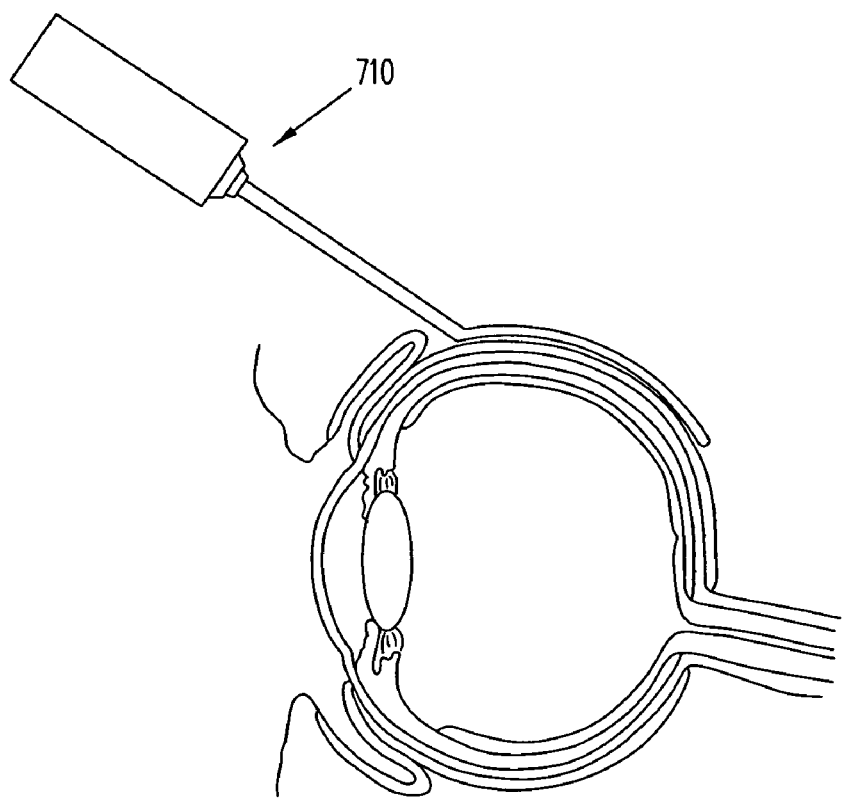
FIG. 7 depicts one delivery system that may be used in the methods described herein.
Figure 8:
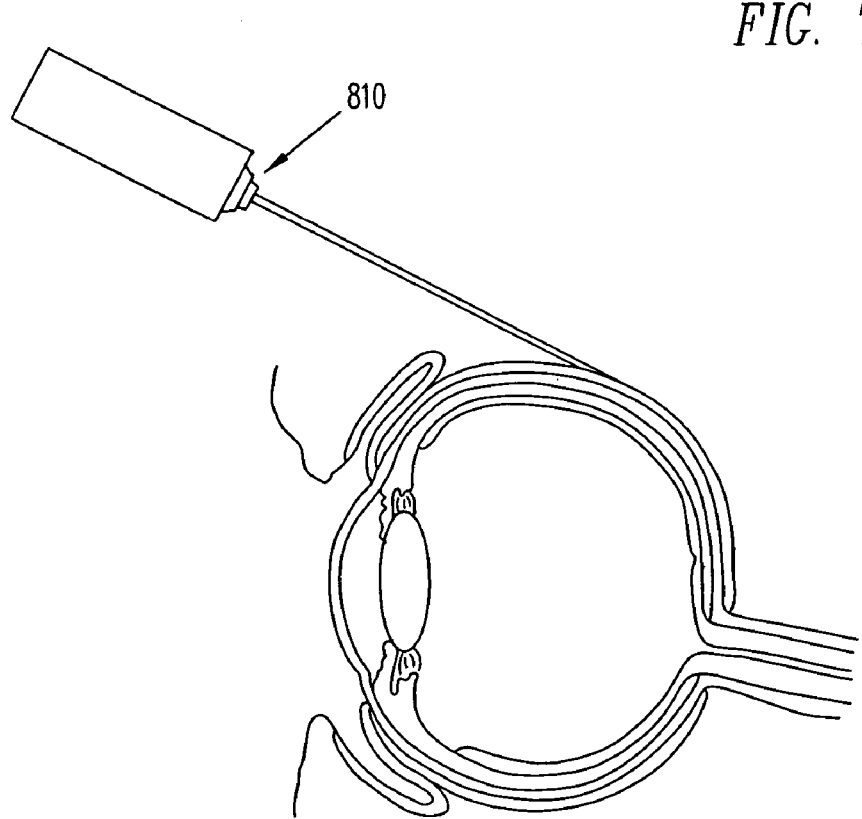
FIG. 8 depicts one delivery system that may be used in the methods described herein.

FIGS. 7 and 8 depict an applicator, injector, or inserter (710) and (810) that may be used for delivery of or various compositions or devices into the posterior subtenons space, including delivery of microspheres or nanoparticles.

Figure 9:
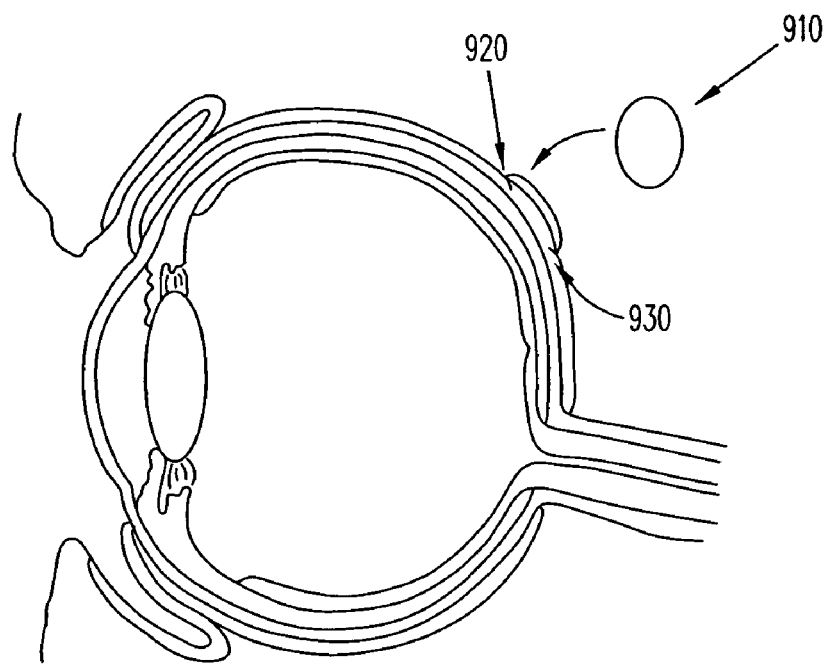
FIG. 9 depicts one delivery system that may be used in the methods described herein.

FIG. 9 depicts a thin film biodegradable polymer with impermeable backing (910) attached to the outer scleral surface (920) by an anchoring surface (930).

Figure 10:
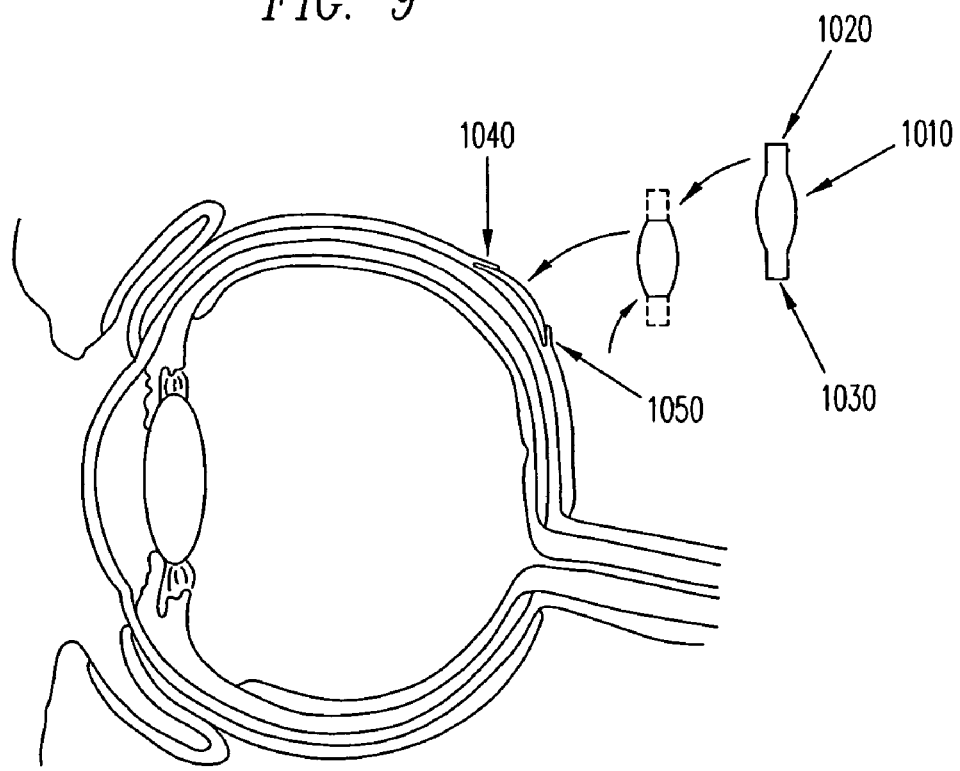
FIG. 10 depicts one delivery system that may be used in the methods described herein.

FIG. 10 depicts a thin film biodegradable polymer with impermeable backing (1010) with scleral flaps (1020 and 1030), which are placed into scleral pockets (1040 and 1050). A 69 blade may be used to cut the scleral pockets.

Figure 11:
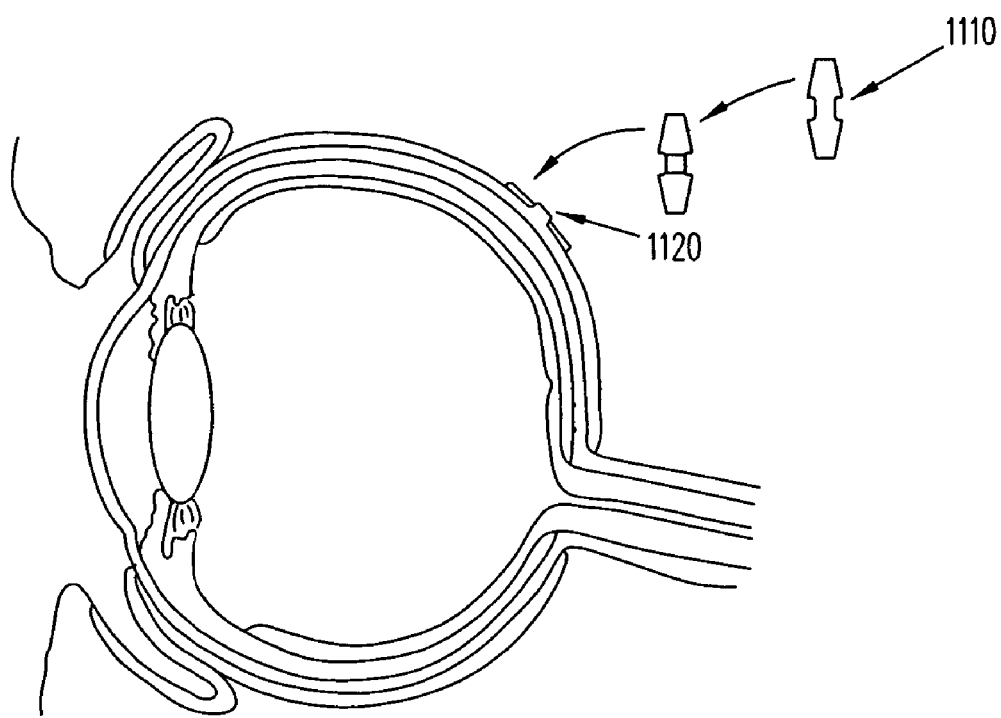
FIG. 11 depicts one delivery system that may be used in the methods described herein.

FIG. 11 depicts a thin film biodegradable polymer with impermeable backing (1110), which is secured to the sclera by placement of the implant (1110) through a "belt loop" cut in the sclera (1120).

Figure 12:
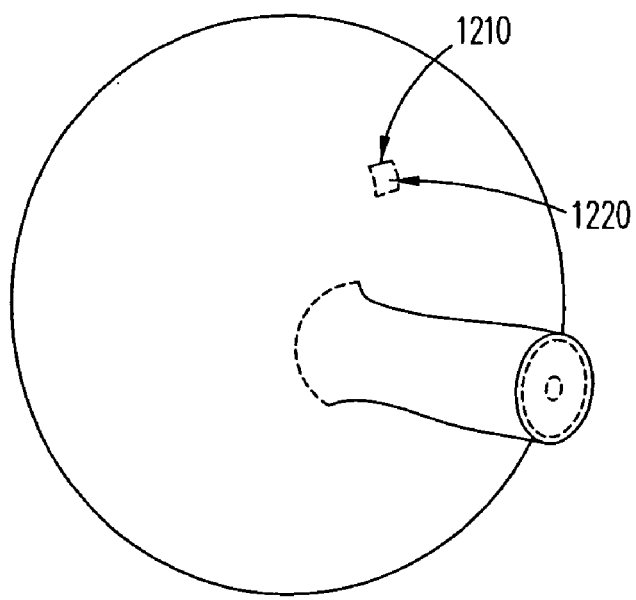
FIG. 12 depicts one delivery system that may be used in the methods described herein.

FIG. 12 depicts a solid core of drug (1210), which is secured to the sclera by placement of the drug into a pocket cut in the sclera (1220).

Figure 13:
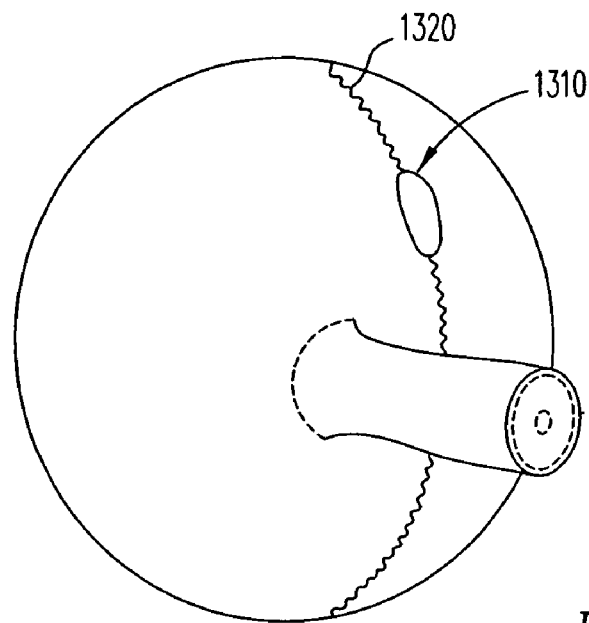
FIG. 13 depicts one delivery system that may be used in the methods described herein.

FIG. 13 depicts a polymer implant (1310), which engages a silicone track delivery system (1320). The silicone track delivery system may be retractable and replaceable. The silicone track delivery system may be attached to recti tendon insertions.

Figure 14:
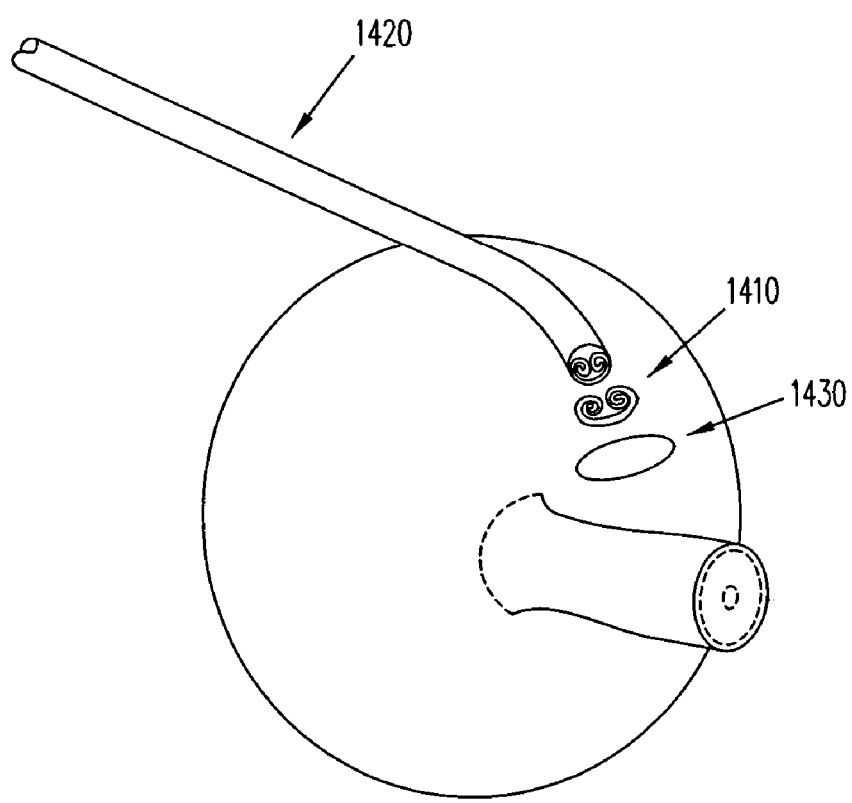
FIG. 14 depicts one delivery system that may be used in the methods described herein.

FIG. 14 depicts a pre-rolled polymer implant (1410), delivered by an injector system (1420), unrolling to provide the polymer implant (1430).

Methods for Placement of the Compositions and Devices

The compositions and devices described herein may be placed in a variety of positions in the ocular region to enable transscleral delivery of the therapeutic agent, including but not limited to subconjunctival placement, intrascleral placement, and subtenons placement.

The compositions and devices may be placed proximate to the outer scleral surface at a location that provides for adequate therapeutic dosing with the least invasive method possible. Subconjunctival placement against the globe will work for such placement. Further posterior placement against the globe may also be used. Access to the globe may be through a variety of means including but not limited to through the bulbar conjunctiva. Using this method of placement, the location of the composition or device may be at or posterior to the external scleral surface corresponding to the ora serrata. The composition or device may also be placed in a location that is posterior to the equator of the eye. The composition or device may also be placed on the sclera near the macula and optic nerve. Other positions of placement are possible and the above descriptions are not limiting on possible placement positions for the compositions and devices.

Once positioned proximate to the outer scleral surface it is preferable that the compositions and devices remain fixed in position so that they continue to deliver therapeutically effective amounts of the therapeutic agent for an expected duration time. Generally, the compositions and devices may be prevented from excessive migration by any method capable of preventing unwanted movement. Non-limiting examples of methods that may be used to prevent excessive migration include shaping of a solid device or solid composition to the contour of the portion of portion of the ocular region into which the solid composition or device is placed, attachment of a solid device to a portion of the ocular region by one or sutures or comparable anchoring means, placement under an extraocular muscle or adjacent to the insertion of an extraocular muscle, attachment of a compositions or solid device to a portion of the ocular region by a bioadhesive layer, and attachment of a solid device to a portion of the ocular region by a surface having a topology capable of anchoring to a portion of the ocular region.

Compositions and devices containing therapeutic agent can be administered directly to the eye using a variety of procedures, including but not limited to procedures in which (1) the therapeutic agent is administered by injection using a syringe and hypodermic needle, (2) a specially designed device is used to inject the therapeutic agent, (3) prior to injection of the therapeutic agent, a pocket is surgically formed within the sclera to serve as a receptacle for the therapeutic agent or therapeutic agent composition. For example, in one administration procedure a surgeon forms a pocket within the sclera of the eye followed by injection of a solution or suspension of the therapeutic agent into the pocket. In another administration procedure a surgeon forms a pocket within the sclera in which a solid implant is inserted. The solid implant may be a solid mass of the therapeutic agent substance or a polymer structure as described above. The scleral pocket can be created by techniques available to those skilled in the practice of vitreoretinal surgery. Alternatively, a specially designed combination of blades and inserters may be utilized for this purpose.

Other administration procedures include, but are not limited to procedures in which (1) a formulation of the therapeutic agent is injected through a specially designed curved cannula to place the therapeutic agent directly against the posterior sclera, (2) a compressed form of the therapeutic agent is placed directly against the sclera inside a scleral flap that is dissected by a surgical procedure on the sclera, (3) the therapeutic agent is inserted into the sclera by a specially designed injector or inserter, (4) a formulation of the therapeutic agent is placed against the scleral surface by a specially designed injector or inserter, (5) the therapeutic agent substance is incorporated within a suture or another solid structure that is sutured onto the eye (any appropriate ocular suturing technique may be used. In one version, the suture has an appropriate ocular or other specific tissue needle swedged on to it. Alternatively, a needle with an eye could be used on a plain filament), (6) a surgeon makes a small conjunctival incision through which to pass a suture and any therapeutic agent delivery structure so as to secure the structure adjacent to the sclera, (7) a surgeon passes the needle directly through the conjunctiva and through external tissue manipulations, brings the entire therapeutic agent delivery structure under the conjunctiva to rest against the sclera, (8) the conjunctiva can be freely moved so that the therapeutic agent delivery structure and suture combination is slightly separated from the conjunctival incision, (9) after therapeutic agent delivery structure insertion, the conjunctiva is closed (the conjunctiva may be closed by any suitable means, such as by suture or glue), and (10) the conjunctiva is left open to accommodate the therapeutic agent delivery structure's size and shape.

In one administration procedure that may be used, a surgeon uses a small hand held device to perform a scleral tunnel dissection. A solid mass or other device or composition of the therapeutic agent substance or composition can then be placed into the sclera.

In one administration procedure that may be used, the device or composition is placed intrascleral. One non-limiting example of such placement is for the device or composition to be placed inside a surgically formed scleral flap. Under such a scenario, either in the clinic, procedure room, or operating room the eye may be prepared in a standard preoperative manner, the sclera will be exposed, and the creation of the flap will be performed with an appropriate blade. A suture may or may not be required.

In one administration procedure that may be used, the device or composition is placed against the surface of the sclera. Under such a scenario, either in the clinic, procedure room, or operating room the eye may be prepared in a standard preoperative manner, the sclera will be exposed, and device or composition placed into position.

Transscleral Delivery of Rapamycin for Treatment of AMD

In one method described herein, rapamycin is transsclerally delivered to prevent, treat, inhibit, delay onset of, or cause regression of angiogenesis in the eye, such as to prevent, treat, inhibit, delay onset of, or cause regression of CNV as observed, for example, in AMD. Rapamycin has been shown to inhibit CNV in rat and mice models, as described in U.S. application Ser. No. 10/665,203, which is incorporated herein by reference in its entirety. Rapamycin has been observed to inhibit Matrigel™ and laser-induced CNV when administered systemically and subretinally. Also, as presented in Example 1 herein, periocular injection of rapamycin inhibits laser-induced CNV.

Other therapeutic agents that may be delivered transsclerally for treatment, prevention, inhibition, delaying onset, or causing regression of angiogenesis in the eye (such as CNV) are members of the limus family of compounds other than rapamycin including but not limited to everolimus and tacrolimus (FK-506).

As described herein, the dosage of the therapeutic agent will depend on the condition being addressed, whether the condition is to be treated, prevented, inhibited, have onset delayed, or be caused to regress, the particular therapeutic agent, and other clinical factors such as weight and condition of the subject and the route of administration of the therapeutic agent. It is to be understood that the methods, devices, and compositions described herein have application for both human and veterinary use, as well as uses in other possible animals. In the case of delivering rapamycin to a human in order to inhibit CNV, one inhibiting amount of the compound has been demonstrated to be one that provides about 10 ng/ml at the tissue level. This concentration of rapaamycin, as well as higher and lower concentrations may be used in the methods described herein. One concentration of rapamycin that may be used in the methods described herein is one that provides about 1 ng/ml or less of rapamycin at the tissue level; another concentration that may be used is one that provides about 2 ng/ml or less at the tissue level, another concentration that may be used is one that provides about 3 ng/ml or less at the tissue level; another concentration that may be used is one that provides about 5 ng/ml or less at the tissue level; another concentration that may be used is one that provides about 10 ng/ml or less at the tissue level; another concentration that may be used is one that provides about 15 ng/ml or less at the tissue level; another concentration that may be used is one that provides about 20 ng/ml or less at the tissue level; another concentration that may be used is one that provides about 30 ng/ml or less at the tissue level; another concentration that may be used is one that provides about 50 ng/ml or less at the tissue level. One of ordinary skill in the art would know how to arrive at the preferred concentration of usage depending on the route and duration of administration utilized.

Delivery of the disclosed therapeutic agents may be delivered at a dosage range of between about 1 picogram/kg/day and about 300 mg/kg/day (with reference to the body weight of the subject), or at dosages higher or lower than this disclosed range, depending on the route and duration of administration. In one device or composition that may be used in the methods herein, the therapeutic agents are delivered at a dosage range of between about 1 picogram/kg/day and about 3 mg/kg/day. Dosages of various therapeutic agents for treating various diseases and conditions described herein can be refined by the use of clinical trials. Additionally, dose ranges include those disclosed in U.S. Pat. Nos. 6,376,517 and 5,387,589, the contents of which are hereby incorporated by reference in their entirety.

In one device that may be used in the methods described herein, rapamycin is incorporated into a solid polymer implant for delivery across the sclera. Based on a flux of rapamycin of 2.4 µg/cm$^2$/day, calculated as discussed herein, approximately 0.8 µg of rapamycin could be delivered daily from a polymer implant presenting approximately 0.33 cm$^2$ surface area to the outer surface of the sclera. This size of structure can be constructed from generally recognized as safe (GRAS) polymers such as PLGA polymers. As used herein, "generally recognized as safe" polymers refers to polymeric material that is currently used in contact with human tissue for a medical purpose, polymeric material that has been shown through animal or human studies to have a low incidence of side effects, or polymeric material that is recognized by medical professionals of ordinary skill in the art as being safe for use in humans. A coiled fiber having the required surface area would have a diameter of about 1 mm and a length of about 4 cm. An appropriately sized elliptical disk would be about 4 mm wide and 1 cm long. The description of these devices is not limiting but is provided by way of example of devices that may be used for delivery of rapamycin.

The solid polymer implants will have a geometry that delivers the therapeutic agent through some area of the outer scleral surface. As described elsewhere herein the requirements for this area will be determined by the concentration of rapamycin maintained at the scleral surface by the device, the permeability of the sclera to the rapamycin, the required flux of rapamycin across the sclera to deliver an effective amount of rapamycin, the duration for which delivery is required, and size restrictions imposed by the portion of the eye into which the device must be placed. One solid polymer implant device that may be used in the methods described herein delivers the therapeutic agent through an area of less than about 1 $cm^2$. Another solid polymer implant device that may be used delivers the therapeutic agent through an area of less than about 0.5 $cm^2$. Another solid polymer implant device that may be used delivers the therapeutic agent through an area of less than about 0.25 $cm^2$. Another solid polymer implant device that may be used delivers the therapeutic agent through an area of between about 0.1 $cm^2$ and about 0.2 $cm^2$. The thickness of the device will depend primarily on the amount of rapamycin that will need to be delivered over the extended period and the size restrictions imposed by the portion of the eye into which the device must be placed. "Thickness" as used in this context means the dimension of the device in the direction approximately normal to the surface presented to the outer scleral surface. Generally, a device with any thickness may be used that is consistent with placement of the device in a particular portion of the eye. One solid polymer implant device that may be used in the methods described herein has a thickness of less than about 2 mm. Another solid polymer implant device that may be used has a thickness of less than about 1 mm.

The devices and compositions described herein may be used for transscleral delivery of therapeutically effective amounts of rapamycin for extended periods of time to treat, prevent, inhibit, delay the onset of, or cause regression of CNV, and thus may be used to treat, prevent, inhibit, delay the onset of, or cause regression of wet AMD. Based on the molecular size, potency, water solubility, stability as a solid, and scleral permeability as demonstrated herein for rapamycin, it has been recognized that rapamycin can likely be delivered transsclerally at therapeutically effective levels for extended periods of time. It is believed that by changing certain characteristics of the devices and compositions described herein, including but not limited to the shape, size, positioning and rapamycin loading in the devices and compositions, the devices and compositions described herein may be used to deliver therapeutically effective amounts of rapamycin transsclerally for a variety of extended time periods including delivery for greater that about 1 week, for greater that about 2 weeks, for greater that about 3 weeks, for greater that about 1 month, for greater that about 3 months, for greater that about 6 months, for greater that about 9 months, for greater that about 1 year, for greater that about 18 months, for greater that about 2 years, for greater that about 3 years, and for greater that about 4 years.

When a therapeutically effective amount of rapamycin is administered to a subject suffering from wet AMD, the rapamycin may treat, inhibit, or cause regression of the wet AMD. Different therapeutically effective amounts may be required for treatment, inhibition or causing regression. A subject suffering from wet AMD may have CNV lesions, and it is believed that administration of a therapeutically effective amount of rapamycin may have a variety of effects, including but not limited to causing regression of the CNV lesions, stabilizing the CNV lesion, and preventing progression of an active CNV lesion.

When a therapeutically effective amount of rapamycin is administered to a subject suffering from dry AMD, it is believed that the rapamycin may prevent or slow the progression of the dry AMD.

EXAMPLES

Unless indicated otherwise, parts are parts by weight, molecular weight is average molecular weight, temperature is in degrees Celsius, and pressure is at or near atmospheric.

Example 1

Inhibition of Laser Induced CNV by Rapamycin

CNV may be induced by rupturing Bruch's membrane with laser. Fifteen mice were given daily periocular injections of 5 micrograms of rapamycin in corn oil vehicle in one eye. After two days of treatment, Bruch's membrane was ruptured by laser at three sites in each eye. The fellow eye served as control and was treated with periocular injections of corn oil only. Two weeks after laser rupture, 10 mice were perfused with fluorescein-labeled dextran and CNV areas were measured in each eye on choroidal flat mounts. The remaining mice had retinas and RPE/choroid dissected and stored at −70° C. for tissue therapeutic agents level measurement.

As depicted in FIG. 1, rapamycin treatment led to a statistically significant reduction in CNV size versus vehicle alone (p=0.0011 by Mann-Whitney U test). The mean CNV area for rapamycin treated eyes was 0.00381 $mm^2$ with a standard deviation of 0.00197 and the vehicle eyes showed a CNV area of 0.00576 $mm^2$ with a standard deviation of 0.00227.

Using HPLC/MS on the retinas of sentinel animals, retinal tissue levels of rapamycin were found to be 25 picograms per milligram tissue in treated eyes and 7 picograms per milligram tissue in control eyes. The animals were found to have rapamycin blood levels of 5.57 nanograms per milligram blood. Thus, although periocular delivery of 5 µg of rapamycin per day in these mice led to clinically significant blood levels, retinal tissue levels were higher in treated eyes than in the fellow control eyes, suggesting transscleral permeation of rapamycin following periocular injection.

This example demonstrates that administration of rapamycin may inhibit CNV.

Example 2

Reversal of Laser Induced CNV by Rapamycin

Fifteen mice had Bruch's membrane ruptured with laser photocoagulation at 3 locations in each eye. After one week, 5 mice were perfused with fluorescein-labeled dextran and the baseline area of CNV was measured in each eye. At that point, the remaining mice were started on daily periocular injections of 5 μl of corn oil containing 5 μg of rapamycin in one eye and corn oil alone in the fellow eye. After one more week, the mice were perfused with fluorescein-labeled dextran and CNV areas were measured in each eye on choroidal flat mounts. The corn oil solution used is approximately a saturated solution. It is expected that lower doses will be used to deliver therapeutically effective amounts of rapamycin.

Figure 2:
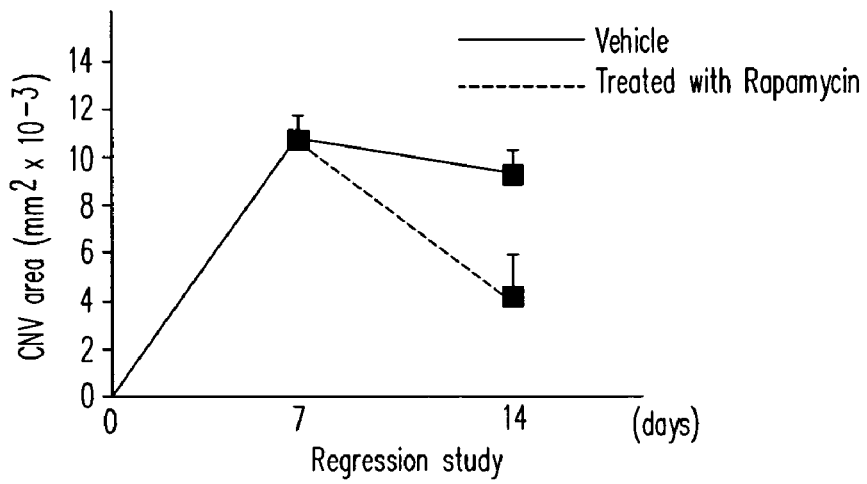
FIG. 2 depicts the reduction of choroidal neovascularization upon periocular injection of rapamycin.

As depicted in FIG. 2, rapamycin treated eyes showed a substantial reduction in CNV area. Baseline lesion CNV area was 0.0105 mm$^2$ with a standard deviation of 0.0037. Untreated eyes had a CNV area of 0.0093 mm$^2$ with a standard deviation of 0.0028. Treated eyes had a CNV area of 0.00458 mm$^2$ with a standard deviation of 0.0053.

This example demonstrates that administration of rapamycin causes regression of CNV.

Example 3

In-Vitro Determination of Flux and Scleral Permeability for Transscleral Rapamycin Delivery A two chamber Ussing type permeability apparatus was used to demonstrate delivery of rapamycin across a human sclera. Prior to testing of sclera, loss of therapeutic agent to the glass walls of the experimental apparatus was evaluated. For the evaluation of loss of drug to the experimental apparatus, the uveal and orbital chambers were exposed to a 2 μg/mL rapamycin solution in balanced salt solution. There was small but significant loss of rapamycin to the apparatus when it was exposed to the 2 μg/mL solution of rapamycin in balanced salt solution.

Transscleral Rapamycin Delivery—DMSO Solution

A 7 mm disk of fresh donor human sclera was used to separate the two chambers of the Ussing permeability apparatus. The two sides of the sclera were denoted "orbital" to represent the outer surface and "uveal" to represent the internal surface. DMSO and methanol dissolves rapamycin readily, however, rapamycin is poorly soluble in aqueous solutions. Thus, in order to grossly replicate a scleral depot delivery system, the hydrophobic therapeutic agent solvents were diluted to 5% concentration in balanced salt solution (BSS) with dissolved rapamycin to form a roughly 100 μg per ml orbital chamber solution. In this example, the chamber on the orbital surface side contained a reservoir of 200 μl of rapamycin dissolved in 5% DMSO in BSS at an expected concentration of 100 μg per milliliter. The 500 μl uveal chamber was continually perfused at 0.0075 milliliter per minute and samples were collected by a fractionater in Eppendorf tubes every 4 hours. The experiment was run for 36 hours.

Figure 3:
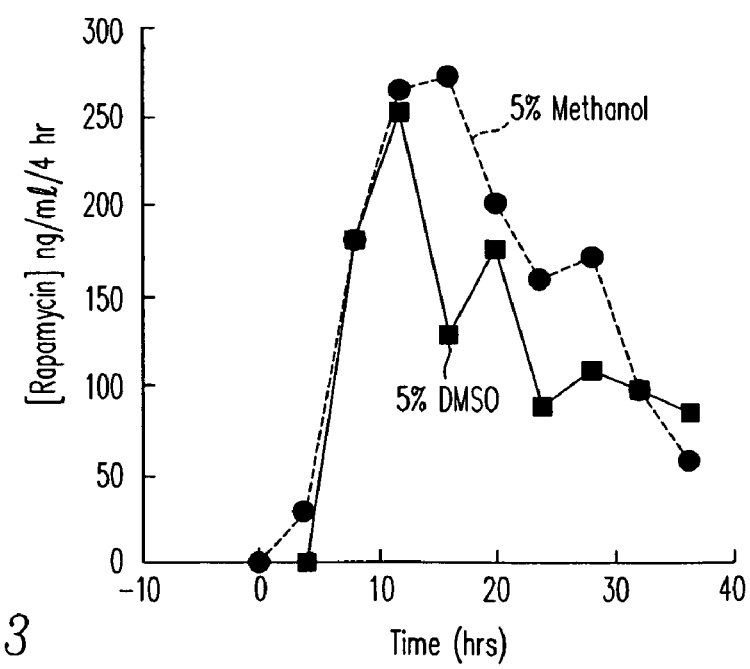
FIG. 3 depicts transscleral permeability of rapamycin as a function of time.
Figure 4:
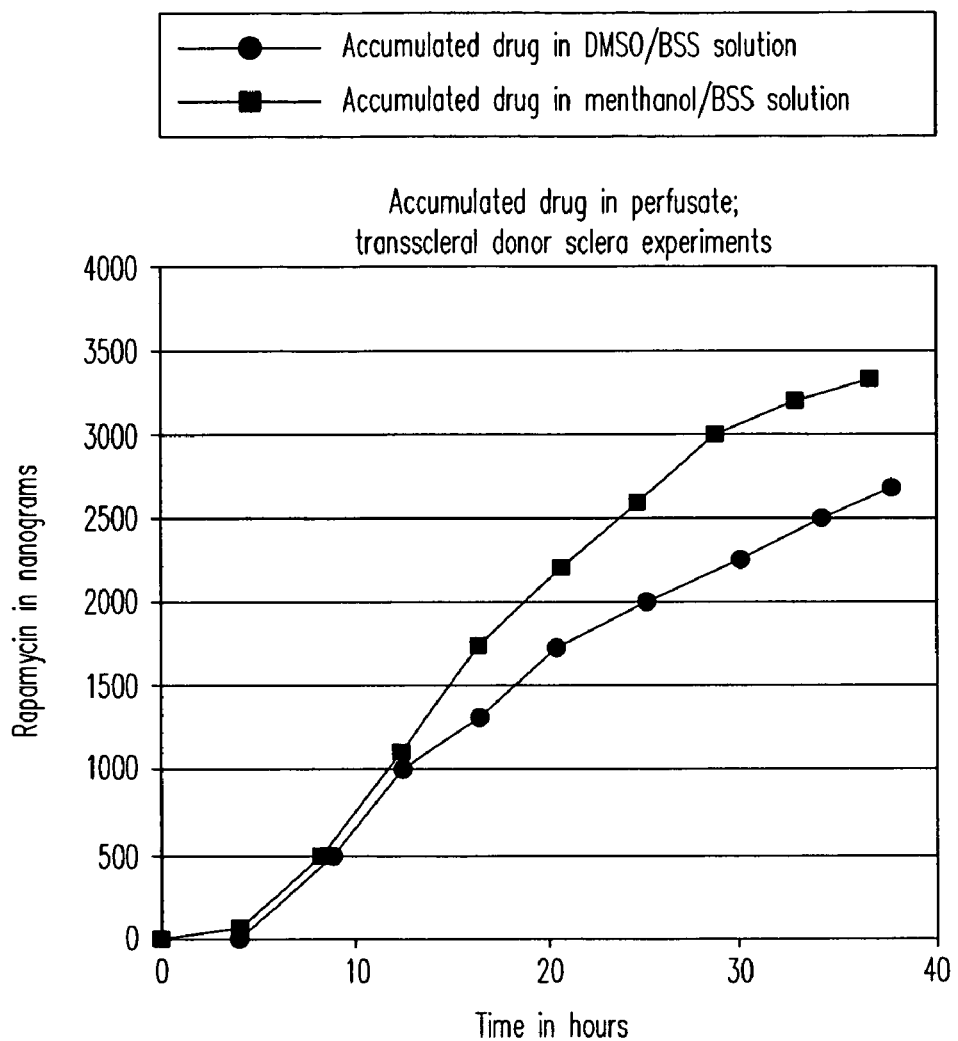
FIG. 4 depicts transscleral accumulation of rapamycin as a function of time.

The time profile of the concentration of rapamycin in the uveal chamber is depicted in FIG. 3 (squares). The peak concentration in the uveal chamber was 250 ng/ml at t=8 to 12 hours. The total amount of rapamycin accumulated on the uveal side of the sclera is depicted as function of time in FIG. 4 (diamonds). The total rapamycin recovered from the uveal chamber was 2.67 micrograms in 36 hours. The sclera was found to hold 0.57 micrograms of rapamycin at the conclusion of the experiment.

The results demonstrated that rapamycin crosses the sclera in amounts significant enough to have a therapeutic effect. At the peak concentrations in the uveal chamber (250 ng/ml), rapamycin will fully dissolve in vitreous. Because the amount of therapeutic agent in the orbital chamber was declining, the steady state was estimated by the highest flux. The highest flux based on this data was 9.35 micrograms per square centimeter per day. A permeability coefficient (K) was calculated as:

$$K_{TRANS} = \frac{\Delta CV}{AtC_0}$$

ΔC represents the increase in concentration the compound in the uveal chamber (0.250 micrograms/ml) that occurs over the interval t, in seconds (1440). V is the chamber volume (1.8 milliliter). A represents the exposed area of the tissue (0.385 cm$^2$). $C_0$ is the initial concentration of the compound in the orbital chamber (92 microgram/ml). Calculated in this manner, the permeability coefficient, K, has the dimensions of cm/s. $K_{TRANS}$ thus expresses the rate at which a given solute traverses the tissue. (*Advanced Therapeutic agent Delivery Reviews* 52 (2001) 37-48 by Dale Geroski and Hank Edelhauser, which is incorporated herein by reference in its entirety). For this experiment $K_{TRANS}$ was roughly 8.82×10$^{-6}$ cm/sec, which was on the order of predictions based on MW. Comparatively, when evaluating the $K_{TRANS}$ of dexamethasone, which is smaller than rapamycin, and adjusting for a lower solubility, the figures for rapamycin are also in the appropriate predicted ranges. It is expected that as the external concentration of rapamycin is raised, the flux will increase. Under the ex-vivo conditions of this example, rapamycin can be delivered in the single digit micrograms per day to the vitreous. Such rates are consistent with therapeutic local tissue levels and support that rapamycin is a viable therapeutic agent for transscleral delivery to the posterior segment for vitreoretinal disease.

Transscleral Rapamycin Delivery—Methanol Solution

The above procedure was followed with the exception that rapamycin was dissolved in 5% methanol in BSS. The time profile of the concentration of rapamycin in the uveal chamber is depicted in FIG. 3 (circles). The peak concentration in the uveal chamber was 271 ng/ml at t=12 to 16 hours. The total amount of rapamycin accumulated on the uveal side of the sclera is depicted as function of time in FIG. 4 (squares). The total rapamycin recovered from the uveal chamber was 3.44 micrograms in 36 hours. The sclera was found to hold 0.41 micrograms at the conclusion of the experiment.

Based on these results, a $K_{TRANS}$ of 9.56×10$^{-6}$ cm/sec was calculated. This rate is consistent with therapeutic local tissue levels indicating that rapamycin is a viable therapeutic agent for transscleral delivery to the posterior segment for treating vitreoretinal disease.

All references cited herein, including patents, patent applications, and publications, are hereby incorporated by reference in their entireties, whether previously specifically incorporated or not.

What is claimed is:

1. A method for treating macular edema in a human, the method comprising administering transsclerally to an eye of the human an amount of rapamycin effective to treat macular edema, wherein the rapamycin is administered transsclerally by placement within or proximate to a sclera of the eye.

2. The method of claim 1, wherein the sclera has an outer scleral surface and the rapamycin is administered transsclerally by placement of a rapamycin containing delivery system proximate to the outer scleral surface.

3. The method of claim 2, wherein the rapamycin containing delivery system comprises a solid rapamycin core.

4. The method of claim 3, wherein the rapamycin containing delivery system further contains a backing portion that is substantially impermeable to rapamycin.

5. The method of claim 2, wherein the rapamycin containing delivery system comprises a suspension of particles of rapamycin.

6. The method of claim 5, wherein the particles of rapamycin have an average diameter of less than about 50 µm.

7. The method of claim 2, wherein the rapamycin containing delivery system comprises rapamycin dispersed in a polymer implant.

8. The method of claim 7, wherein the polymer implant is a biodegradable polymer implant.

9. The method of claim 7, wherein the polymer implant is a non-biodegradable polymer implant.

10. The method of claim 8 or claim 9, wherein the polymer implant further comprises a rapamycin impermeable backing.

11. The method of claim 8 or claim 9, wherein the polymer implant is shaped as a suture.

12. The method of claim 11, wherein the suture has a length of less than about 10 cm and a diameter of less than about 2 mm.

13. The method of claim 8 or claim 9, wherein the polymer implant is shaped as a coiled fiber.

14. The method of claim 13, wherein the coiled fiber has a length of less than about 5 cm and a diameter of less than about 1 mm.

15. The method of claim 8 or claim 9, wherein the polymer implant is shaped as a disk.

16. The method of claim 8 or claim 9, wherein the polymer implant has a scleral surface portion for placement on the outer scleral surface of the eye and the scleral surface portion has an area through which the rapamycin is delivered to the outer scleral surface of less than about 0.5 $cm^2$.

17. The method of claim 8 or claim 9, wherein the polymer implant has a scleral surface portion for placement on the outer scleral surface of the eye, and the scleral surface portion comprises a bioadhesive layer.

18. The method of claim 8 or claim 9, wherein the polymer implant has a scleral surface portion comprises a number of protrusions, and whereby the scleral surface portion of the polymer implant anchors the polymer implant to the outer scleral surface of the eye.

19. The method of claim 8 or claim 9, wherein the polymer implant comprises a rapamycin containing portion coated with a coating, and wherein the concentration of rapamycin in the coating is less than the concentration of rapamycin in the rapamycin containing portion.

20. The method of claim 19, wherein the concentration of rapamycin in the coating is such that release of rapamycin from the coating does not deliver a wound healing inhibiting amount of rapamycin.

21. The method of claim 2, wherein the rapamycin containing delivery system comprises rapamycin dissolved in a solvent.

22. The method of claim 2, wherein the rapamycin containing delivery system delivers the rapamycin transsclerally in an amount sufficient to maintain an amount effective to treat macular edema for an extended period of time.

23. The method of claim 22, wherein the rapamycin containing delivery system delivers the rapamycin transsclerally in an amount sufficient to treat macular edema for at least about three weeks.

24. The method of claim 2, claim 5, or claim 21, wherein the rapamycin is administered transsclerally to the eye by subconjunctival or subtenon placement of the rapamycin containing delivery system.

25. The method of claim 24, wherein the rapamycin is administered transsclerally to the eye by subconjunctival injection of the rapamycin containing delivery system.

26. A method for treating macular edema in a human, comprising administering a composition to an eye of the human by subconjunctival or subtenon placement of the composition, wherein the composition comprises an amount of rapamycin effective to treat macular edema.

27. The method of claim 26, wherein the composition comprises a suspension of particles of rapamycin.

28. The method of claim 26, wherein the composition comprises rapamycin dissolved in a solvent.

29. The method of claim 21 or claim 28, wherein the solvent comprises polyethylene glycol.

30. The method of claim 29, wherein the solvent further comprises ethanol.

31. The method of claim 27 or claim 28, wherein the composition is administered to the eye by subconjunctival injection.

* * * * *

UNITED STATES PATENT AND TRADEMARK OFFICE
CERTIFICATE OF CORRECTION

PATENT NO. : 7,585,517 B2 Page 1 of 1
APPLICATION NO. : 10/945682
DATED : September 8, 2009
INVENTOR(S) : Cooper et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1071 days.

Signed and Sealed this

Fourteenth Day of September, 2010

David J. Kappos
*Director of the United States Patent and Trademark Office*